United States Patent
Conway et al.

(10) Patent No.: US 7,341,992 B2
(45) Date of Patent: Mar. 11, 2008

(54) LECTIN-LIKE DOMAIN OF THROMBOMODULIN AND ITS THERAPEUTIC USE

(75) Inventors: Edward M. Conway, Overijse (BE); Désiré Collen, Winksele (BE)

(73) Assignees: Vlaams Interuniversitair Instituut Voor Biotechnologie VZW, Zwijnaarde (BE); D. Collen Research Foundation, Leuven (BE)

( * ) Notice: Subject to any disclaimer, the term of this patent is extended or adjusted under 35 U.S.C. 154(b) by 332 days.

(21) Appl. No.: 10/478,360

(22) PCT Filed: May 24, 2002

(86) PCT No.: PCT/EP02/05727

§ 371 (c)(1),
(2), (4) Date: Feb. 10, 2004

(87) PCT Pub. No.: WO02/096947

PCT Pub. Date: Dec. 5, 2002

(65) Prior Publication Data

US 2005/0014220 A1    Jan. 20, 2005

(30) Foreign Application Priority Data

May 25, 2001 (EP) .................. 01201979

(51) Int. Cl.
*A61K 38/16* (2006.01)

(52) U.S. Cl. .......................................... 514/8

(58) Field of Classification Search .............. None
See application file for complete search history.

(56) References Cited

U.S. PATENT DOCUMENTS 6,500,646 B1 * 12/2002 Kuriyama et al. ......... 435/69.7
2004/0077552 A1 * 4/2004 Luger ......................... 514/18

FOREIGN PATENT DOCUMENTS

EP        1 390 407           9/2005
JP        2000053582 A   *   2/2000

* cited by examiner

*Primary Examiner*—Cecilia Tsang
*Assistant Examiner*—Thomas S. Heard
(74) *Attorney, Agent, or Firm*—Knobbe, Martens, Olson & Bear, LLP

(57) ABSTRACT

The in vivo role of the N-terminal lectin-like domain of thrombomodulin was studied by using homologous recombination in murine ES cells to create mutant mice that lack this region of thrombomodulin. Phenotypic analysis shows that said mice respond identically to their wild type littermates following pro-coagulant challenges meaning that the protein C pathway is not altered by the mutation. However, following several inflammatory stimuli, it was observed that the mutant mice showed an elevated neutrophil extravasation in several organs. It is found that leukocyte adhesion could be abrogated by addition of recombinant lectin-domain meaning that said domain has direct anti-inflammatory properties which means that the lectin-like domain can be used to manufacture a medicament useful for the treatment of a variety of inflammatory disease processes.

9 Claims, 2 Drawing Sheets

Figure 1

Figure 2:
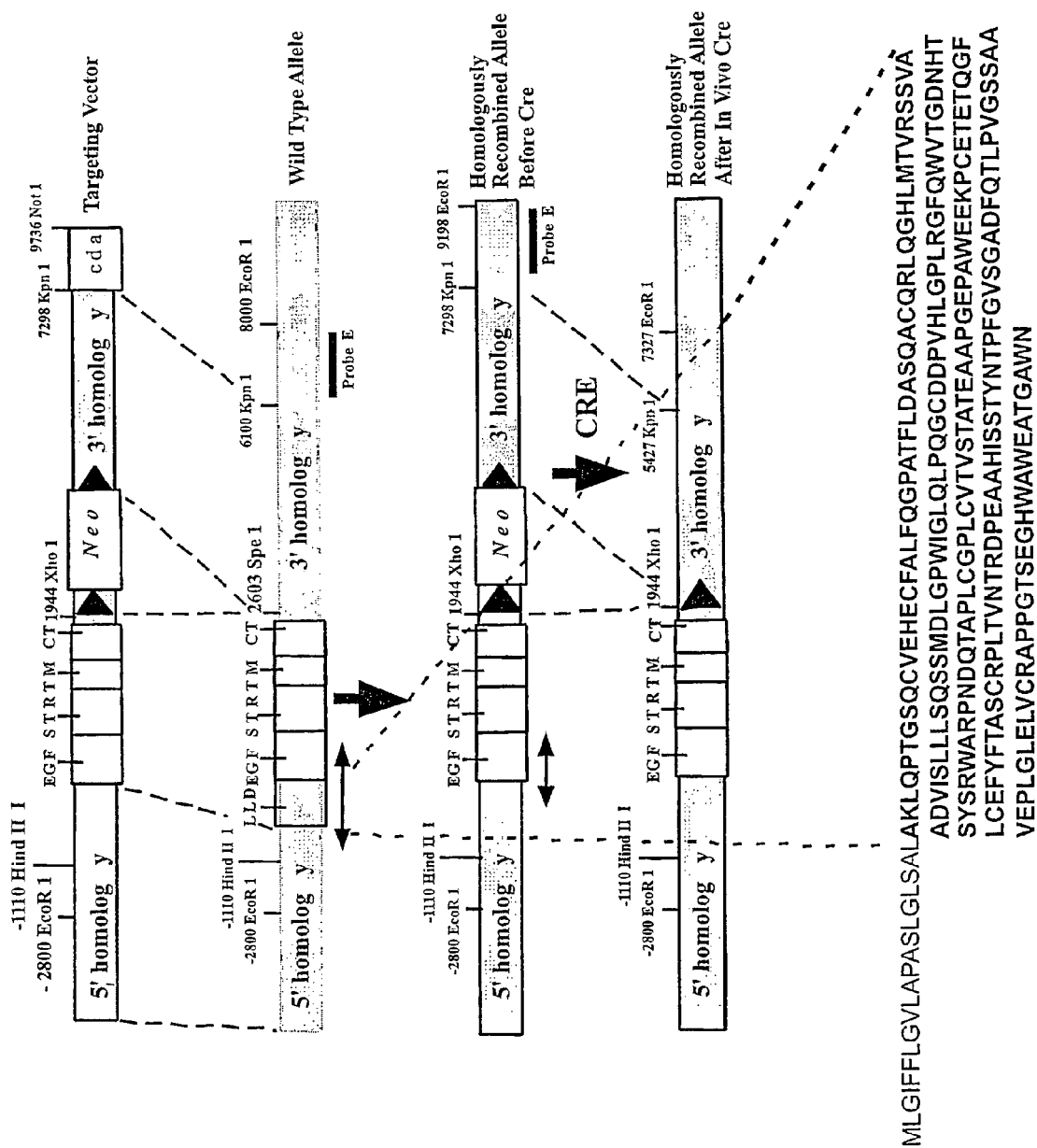

```
                    10                  20                       30
hTMaa    M L G V L V L G A L A L A G L G F P A A E P Q P G G S Q C
mTMaa    M L G I F F L G V L A P A S L G L S A L A K L Q P T G S Q C
         M L G       L G     L A     L G     A     A     Q P   G S Q C 40                  50                       60
hTMaa    V E H D C F A L Y P G P A T F L N A S Q I C D G L R G H L M
mTMaa    V E H E C F A L F Q G P A T F L D A S Q A C Q R L Q G H L M
         V E H . C F A L .   G P A T F L   A S Q     C       L . G H L M 70                  80                       90
hTMaa    T V R S S V A A D V I S L L L N G D G G V G R R R L W I G L
mTMaa    T V R S S V A A D V I S L L L S Q S S - - M D L G P W I G L
         T V R S S V A A D V I S L L L                         W I G L 100                 110                      120
hTMaa    Q L P P G C G D P K R L G P L R G F Q W V T G D N N T S Y S
mTMaa    Q L P Q G C D D P V H L G P L R G F Q W V T G D N H T S Y S
         Q L P   G C   D P     L G P L R G F Q W V T G D N . T S Y S 130                 140                      150
hTMaa    R W A R L D L N G A P L C G P L C V A V S A A E A T V P S E
mTMaa    R W A R P N D Q T A P L C G P L C Y T V S T A T E A A P G E
         R W A R         A P L C G P L C V . V S . A   .   P   E 160                 170                      180
hTMaa    P I W E E Q Q C E V K A D G F L C E F H F P A T C R P L A V
mTMaa    P A W E E K P C E T E T Q G F L C E F Y F T A S C R P L T V
         P   W E E .   C E   .     G F L C E F   F   A . C R P L . V 190                 200                      210
hTMaa    E P G - A A A A V S I T Y G T P F A A R G A D F Q A L P V
mTMaa    N T R D P E A A H I S S T Y N T P F G V S G A D F Q T L P V
                 A A   .   S   T Y . T P F       G A D F Q . L P V 220                 230                      240
hTMaa    G S S A A V A P L G L Q L M C T A P P G A V Q G H W A R E A
mTMaa    G S S A A V E P L G L E L V C R A P P G T S E G H W A W E A
         G S S A A V   P L G L . L . C   A P P G .   . G H W A   E A 250                 260                      270
hTMaa    P G A W D C S V E N G G C E H A C N A I P G A P R C Q C P A
mTMaa    T G A W N C S V E N G G C E Y L C N R S T N E P R C L C P R
           G A W   C S V E N G G C E     C N               P R C   C P
```

LECTIN-LIKE DOMAIN OF THROMBOMODULIN AND ITS THERAPEUTIC USE

RELATED APPLICATIONS

This application is the U.S. National Phase under 35 U.S.C. § 371 of International Application PCT/EP02/05727, filed May 24, 2002, which claims priority of EP 01201979.0, filed May 25, 2001 Each of the above applications are incorporated herein by reference in their entirety.

FIELD OF THE INVENTION

The present invention relates to the lectin-like domain of thrombomodulin and its use for the prevention and/or the treatment of diseases such as inflammatory disorders.

BACKGROUND OF THE INVENTION

Although it has long been recognized that the coagulation system plays a role in modulating inflammation, it is only recently that the impact of this contribution has been appreciated and that some of the molecular links have been established. In this respect, the protein C anticoagulant pathway is particularly relevant. In addition to its well-characterized role in modulating thrombin generation, this system, composed of a complex of soluble and membrane-associated proteins, plays an integral part in regulating the response to selected inflammatory agents (reviewed in[44]). Substantial clinical data have revealed that patients with severe sepsis have significantly diminished levels of protein C and protein S, and the extent of suppression of protein C may correlate with clinical outcome[49]. Activated protein C (APC) appears to modulate the inflammatory response by several mechanisms, including inhibiting polymorphonuclear cell (PMN) activation and elastase release, blocking PMN interactions with selecting, and preventing cytokine release by monocytes[48,52-55]. More recently, the endothelial cell protein receptor (EPCR), a cofactor that enhances activation of protein C by thrombin-thrombomodulin, has also been found to modulate the function of APC in inflammation. Moreover, inhibition of the interaction of APC/PC with EPCR in vivo resulted in an increased inflammatory response following E. coli infusions in baboons[56]. Further links between EPCR and inflammation, although not yet fully delineated, are being explored as Esmon and coworkers have reported that a soluble form of EPCR is released during sepsis[57], interferes with activation of protein C, and binds to a receptor on activated neutrophils that is the autoantigen in Wegener's granulomatosis[58,59]. Another particularly relevant player in the anticoagulant system is thrombomodulin (TM), a critical cofactor in the activation of protein C, and a widely expressed glycoprotein receptor for thrombin. With the cloning and sequencing of the gene for thrombomodulin[1], the putative structural organization of the protein and the regions responsible for its anticoagulant and anti-fibrinolytic function have been elucidated. Mature single-chain TM in the human is 557 amino acids long and is structurally divided into five domains. The N-terminal region (residues 1-226) [2] has a module (residues 1-154) with homology to the lectin domains of the hepatic asialoglycoprotein receptor and IgE, as well as to members of the selectin family. Although controversial, in vitro analyses suggest that this domain is required for constitutive internalization of the receptor in some cells[5,6]. From residues 155 to 226, there is a hydrophobic region which may be associated with the plasma membrane and which contains two potential sites for O-linked glycosylation. The next domain is comprised of six epidermal growth factor (EGF)-like repeats, the last 3 or 4 of which are necessary for activation of TAFI or protein C, respectively, by thrombin. The function of the other EGF-like repeats is unknown. The third domain between the EGF-like repeats and the membrane-spanning region is serine/threonine rich and contains four potential sites for O-linked glycosylation, to one of which is attached a chondroitin sulfate, important for full anticoagulant activity of TM. Fourthly, there is a highly conserved transmembrane domain, and fifthly a short cytoplasmic tail that contains potential sites of phosphorylation, and a single cysteine that may mediate multimerization of the molecule. It has been shown that TM is important in regulating the inflammatory process via the anticoagulant pathway. The downregulation of vascular endothelial cell TM by inflammatory cytokines—an effect mirrored by the expression of cellular EPCR—directly impairs the generation of APC. The protein C co-factor function of TM is also impaired in the face of inflammation, as activated PMNs release lysosomal proteases and oxidants that result in proteolysis of the receptor and oxidation of a critical methionine within the EGF-like repeats of TM that inactivates the function of glycoprotein for protein C activation. Several additional lines of evidence support a role for TM as an anti-inflammatory agent. Recombinant soluble forms of TM, most of which were composed of the entire extramembranous regions, were used to prevent endotoxin-induced pulmonary accumulation of leukocytes and ARDS, organ failure, or lethality in small animal models[54,63,64]. Adenovirus-mediated gene transfer of TM in a rabbit restenosis model was not only effective in reducing restenosis, but also resulted in decreased inflammation and extravasation of leukocytes[22]. In a spinal cord compression-induced injury model in rats, recombinant soluble TM provided neuroprotection, with reduction in leukocyte accumulation and cytokine mRNA expression[65]. In each of these studies, the improved outcomes following TM administration were attributed to enhanced activation of protein C, while the possibility that other domains of TM might contribute to the apparent anti-inflammatory effect was never considered. In the present invention we have determined the in vivo function of the N-terminal lectin-like domain of TM by generating mice lacking this domain and we have shown that addition of the recombinant N-terminal lectin-like domain provides the vascular endothelium with natural anti-inflammatory properties by interfering with leukocyte adhesion. (1) TM is a known molecule, (2) the EGF-regions of TM are known to have anti-coagulant (and indirectly anti-inflammatory) activity. However, the current invention surprisingly demonstrates that the lectin-like region of TM has an anti-inflammatory function. Indeed, since it has been shown in the art that several members of the C-type lectin family (to which the lectin-like domain of TM belongs) function to enhance leukocyte adhesion one would expect that the lectin-like domain of TM has rather a pro-inflammatory function.

FIGURE AND TABLE LEGENDS

FIG. 1: An alignment of the first 269 N-terminal amino acid residues of human TM (hTM) with the first 268 N-terminal amino acid residues of murine TM. Identical residues are shown in each third row. The region that was deleted in the TM$^{Led/Led}$ mice (lacking the putative N-terminal signal peptide) is boxed and is 223 amino acid residues long. Murine thrombomodulin fragment (mTM$_{lec155}$) extends 155 residues from 3 amino acid residues after the putative signal peptide (solid arrow) until ending with the sequence ". . . CRP" at the dashed vertical line. Murine thrombomodulin fragment TM$_{lec223}$ extends 223 residues from 3 amino acid residues after the signal peptide to end with the sequence ". . . GAWD". Human thrombomodulin fragment (hTM$_{lec226}$), SEQ ID NO: 1, extends 224 residues from 4 amino acids after the putative signal peptide (dashed arrow) until ending with the sequence ". . . GAWD". Human thrombomodulin fragment (hTM$_{lec154}$) extends 157 residues from 4 amino acid residues after the putative signal peptide (dashed arrow) until ending with the sequence ". . . CRP" at the dashed vertical line.

FIG. 2: Schematic overview of the construction of the targeting vector to delete the N-terminal domain of thrombomodulin. A detailed description can be found in materials and methods, section 2.

Table 1: Response of mice exposed to hypoxia. Lung tissue levels of fibrin and plasma levels of FPA with associated SD. No significant differences between TMLeD/LeD and TMwt/wt mice were demonstrated (p>0.1).

Table 2: Response of mice exposed to LPS. Lung tissue levels of fibrin with associated SD. No significant differences between TMLeD/LeD and TMwt/wt mice were demonstrated (p>0.1).

Table 3: Response of mice exposed to sublethal dose of LPS. Serum cytokine levels were measured, as were peripheral white blood cell (WBC) counts. TNFα and IL-1β levels are significantly higher in TMLeD/LeD and TMLeDneo/LeDneo mice. For each group, n=18.

Table 4: Myeloperoxidase (MPO) activity in BALF after LPS inhalation. MPO activity is significantly higher in lungs of TM$^{LeD/LeD}$ mice after LPS exposure. Results are representative of an experiment performed twice.

Table 5: Plasma levels of human protein C (hPC) and human activated protein C (hAPC) following infusion of hPC as described in methods. The results reflect one of two representative experiments, each of which had 5 mice in each group.

Table 6: Bone marrow derived PMNs from either genotype mice were assessed for adhesion to fEND.5 cells in a flow chamber model. Results reflect results of 5 independent experiments. For each experiment, 15 microscopic fields were counted as detailed in methods.

Table 7: Bone marrow derived PMNs from either genotype mice were assessed for adhesion to fEND.5 cells in a flow chamber model. Results reflect results of 5 independent experiments. For each experiment, 15 microscopic fields were counted as detailed in methods.

Table 8: Static adhesion assay. PMN and lymphocyte adhesion was significantly greater to non-TNF treated TM$^{LeD/LeD}$ endothelial cells than to TM$^{wt/wt}$ endothelial cells (p<0.005). Anti-TM antisera (ab) increased PMN adhesion in TM$^{wt/wt}$ endothelial cells (p<0.005), but had no additional effect on PMN adhesion to TM$^{LeD/LeD}$ endothelial cells. This is a representative experiment performed 3 times, on 3 different clones each. For each experiment, 5 wells were used for each condition, and adherent leukocytes in 15 microscopic fields were counted.

Table 9: Effect of recombinant TM$_{lec155}$ on PMN adhesion. PMNs were derived from wild-type mice. TM$_{lec155}$ significantly decreased PMN adhesion to TM$^{LeD/LeD}$ endothelial cells.

Table 10: Effect of recombinant TM$_{lec155}$ on cytokine response in vivo. Wild-type mice were treated with LPS 20 μg/gm i.p., following 5 min later with the noted treatment. Plasma levels of IL-1b were measured 3 hours later

AIMS AND DETAILED DESCRIPTION OF THE INVENTION

Thrombomodulin is a widely expressed glycoprotein receptor that plays a physiologically important role in maintaining normal hemostatic balance post-natally. In previous studies it has been shown that inactivation of the TM gene in mice resulted in embryonic lethality without thrombosis. In the present invention the in vivo role of the N-terminal lectin-like domain of TM was studied by using homologous recombination in ES cells to create mice that lack this region of TM (TM$^{LeD/LeD}$). Cross-breeding of F1 TM$^{wt/LeD}$ mice (1 wild-type and 1 mutant allele) resulted in over 300 healthy offspring with a normal Mendelian inheritance pattern, indicating that the lectin-like domain of TM is not necessary for normal fetal development. We have shown that the TM$^{LeD/LeD}$ mice responded identically to their wild-type littermates following pro-coagulant challenges meaning that activation of protein C was not altered by the specific mutation in TM. However, following LPS stimulation, TM$^{LeD/LeD}$ mice responded with significantly heightened plasma levels of TNFα and IL-1β (p<0.001) as compared to their wild-type counterparts. Baseline neutrophil accumulation in lung, liver and kidneys were elevated in the TM$^{LeD/LeD}$ mice, while peripheral leukocyte counts were normal. Using flow chamber and static adhesion models, adhesion of bone marrow-derived leukocytes from TM$^{LeD/LeD}$ or TM$^{wt/wt}$ mice to vascular endothelial cells from TM$^{LeD/LeD}$ mice, ±TNFα exposure, was enhanced 3-5-fold (p<0.05) as compared to adhesion to endothelial cells from wild-type mice. Adhesion could be abrogated by addition of recombinant lectin-domain. Enhanced ICAM-1 mRNA and protein was detected in both the vascular endothelial cells and lungs from the TM$^{LeD/LeD}$ mice. In the present invention we thus demonstrate that the lectin-like domain of TM has direct anti-inflammatory properties that are relevant in the progression of a variety of inflammatory disease processes.

In a first embodiment the invention provides a polypeptide consisting essentially of an amino acid sequence corresponding to SEQ ID NO: 1 or fragments or homologues thereof for use as a medicament. SEQ ID NO: 1 represents an amino acid sequence corresponding with 224 amino acids of human thrombomodulin. In a further embodiment the invention provides fragments of SEQ ID NO: 1 such as SEQ ID NO: 2, 3, 4, 5, 6, 7 and 8 for use as a medicament. SEQ ID NO: 2 consists of 1-157 amino acids of SEQ ID NO: 1, SEQ ID NO: 3 consists of 3-33 amino acids of SEQ ID NO: 1, SEQ ID NO: 4 consists of 33-159 amino acids of SEQ ID NO: 1, SEQ ID NO: 5 consists of 18-40 amino acids of SEQ ID NO: 1, SEQ ID NO: 6 consists of 47-56 amino acids of SEQ ID NO: 1, SEQ ID NO: 7 consists of 84-97 amino acids of SEQ ID NO: 1 and SEQ ID NO: 8 consists of 81-118 amino acids of SEQ ID NO: 1. To clarify the polypeptide sequences for which protection is sought in this patent application we refer to FIG. 1. FIG. 1 shows an alignment of the first 269 amino-terminal amino acids of human thrombomodulin (hTM) with the first 268 amino-terminal amino acid residues of murine thrombomodulin (mTM).

Alternatively based on computer predictions of the 3-dimensional structure of the N-terminal lectin-like domain of TM (*J. Mol. Model.* (1998) 4, 310), fragments of SEQ ID NO:1, comprising a minimal lectin-like domain of thrombomodulin, can also be generated. Polypeptide sequences can be made by chemical polypeptide synthesis as known in the art or alternatively by recombinant means. The murine $TM_{lec223}$ is 67% identical at the amino acid level to the corresponding region of human TM. An additional 9% of the residues are considered similar. The murine $TM_{lec155}$ is 69% identical at the amino acid level to the corresponding region of human TM. An additional 8% of the residues are considered similar. The putative signal peptide (site of cleavage shown on FIG. 1 with a dashed arrow) for human TM probably encompasses the first 18 amino acid residues of the "pre-protein" deduced from the cDNA sequence. This is also based on N-terminal sequencing of soluble forms of TM detected in human plasma and urine. Consequently, numbering has generally been based on that information, with number 1 corresponding to amino acid 19 of the "pre-protein" (including the signal peptide), i.e. starting from APAEP . . . Similar information is lacking for murine TM. Based on computer analyses (PSORT http://psort.nibb.ac.jp/form.html), the putative signal peptide for murine TM encompasses the first 17 amino acids of the "pre-protein" (site of cleavage shown on FIG. 1 with solid arrow). Thus, investigators have generally assigned the first amino acid of the protein to start on the 18th amino acid, i.e. from SALAKL . . . The wording 'fragments' as used herein means polypeptides of at least 10, at least 15, at least 20, at least 25, at least 30, at least 35, at least 40, at least 45, at least 50, at least 55, at least 60 or at least 65 contiguous amino acids that are derived from SEQ ID NO:1.

The term 'homologues' means homology at the amino acid level. Homologues should be at least 65%, 70%, 75%, 80%, 85%, 90% or 95% homologous with SEQ ID NO: 1, 2, 3, 4, 5, 6, 7 or 8. Homology is determined using default parameters of a DNA sequence analysis software package developed by the Genetic Computer Group (GCG) at the University of Wisconsin.

It is clear that the tertiary structure of the entire lectin-like domain is likely to be critically important for its anti-inflammatory function. Therefore, recombinant lectin-like domain can be purified to perform X-ray christallography and this information can be valuable for a person skilled in the art to introduce mutations or deletions to enhance the inflammatory function of the lectin-like domain or to obtain fragments of the lectin-like domain with inflammatory function.

In the present invention we have determined that transgenic mice lacking the N-terminal domain of TM, yet with normal antigenic levels of TM ($TM^{Led/Led}$ mice), have an enhanced response to lipopolysaccharides (LPS), shortened survival times and significantly elevated serum cytokine levels. It was found that the $TM^{Led/Led}$ mice had apparently no hypercoagulable disorder which indicates that the protein C anticoagulant pathway is intact. Nonetheless, to definitively distinguish the anti-inflammatory effects of APC from those related to loss of the N-terminal domain of TM, it was necessary to absolutely exclude the possibility that protein C activation was impaired in the $TM^{Led/Led}$ mice. To this end, we confirmed that in wild-type and $TM^{Led/Led}$ mice, the antigenic and functional cell-surface expression of TM, the latter with respect to thrombin-dependent activation of protein C, were similar by: (1) quantitating tissue levels of TM, (2) assaying cell surface functional levels of TM in lymphatic and vascular endothelial cells derived from the mice, and (3) by quantitatively determining the capacity of intact vascular endothelial TM to activate exogenous human protein C before and after LPS exposure. These measures established that the TM-dependent anticoagulant properties, and specifically the function of EGF-like domains 3-6 in the $TM^{Led/Led}$ mice were intact, and that APC levels were not significantly altered by deletion of the N-terminal domain. Although the $TM^{Led/Led}$ mice lack both the lectin-like domain and the adjacent hydrophobic region, it is clear that the anti-inflammatory function resides within the lectin-like domain of TM, since we show that in static adhesion assays, PMN adhesion can be abrogated by the addition recombinant $TM_{lec155}$ which does not contain the hydrophobic region.

Therefore in another embodiment it is clear that SEQ ID NO:1, 2, 3, 4, 5, 6, 7 or 8 or homologues or fragments thereof can be efficiently used for the manufacture of a medicament to prevent and/or to treat inflammation. It has to be understood that homologues or fragments which are structurally defined above should be capable, when used for the manufacture of a medicament, to prevent and/or to treat inflammation. The activity of fragments can be efficiently measured in for example flow chamber experiments or static adhesion assays as described herein. It is also understood that peptidomimetics of especially the smaller peptides (SEQ ID 3, 5, 6 and 7) can be used for the manufacture of a medicament to prevent and/or to treat inflammation. The term 'peptido mimetic' means a molecule able to mimic the biological activity of a peptide but is no longer peptidic in chemical nature. By strict definition, a peptidomimetic is a molecule that no longer contains any peptide bonds (that is, amide bonds between amino acids). However, the term peptide mimetic is sometimes used to describe molecules that are no longer completely peptidic in nature, such as pseudo-peptides, semi-peptides and peptoids. Whether completely or partially non-peptide, peptidomimetics according to this invention provide a spatial arrangement of reactive chemical moieties that closely resembles the three-dimensional arrangement of active groups in the peptide on which the peptidomimetic is based. As a result of this similar active-site geometry, the peptidomimetic has effects on biological systems, which are similar to the biological activity of the peptide. The peptidomimetic of this invention are preferably substantially similar in both three-dimensional shape and biological activity to the peptides set forth above. Substantial similarity means that the geometric relationship of groups in the peptide that react with for example a type I transmembrane protein is preserved. There are clear advantages for using a mimetic of a given peptide rather than the peptide itself, because peptides commonly exhibit two undesirable properties: (1) poor bioavailability; and (2) short duration of action. Peptide mimetics offer an obvious route around these two major obstacles, since the molecules concerned are small enough to be both orally active and have a long duration of action. There are also considerable cost savings and improved patient compliance associated with peptide mimetics, since they can be administered orally compared with parenteral administration for peptides. Furthermore, peptide mimetics are much cheaper to produce than peptides. Finally, there are problems associated with stability, storage and immunoreactivity for peptides that are not experienced with peptide mimetics. The peptides described in the present invention have utility in the development of such small chemical compounds with similar biological activities and therefore with similar therapeutic utilities. The techniques of developing peptidomimetics are conventional. Thus, peptide bonds can be replaced by non-peptide bonds that allow the peptidomimetic to adopt a similar structure,.and therefore biological activity, to the original peptide. Further modifications can also be made by replacing chemical groups of the amino acids with other chemical groups of similar structure. The development of peptidomimetics can be aided by determining the tertiary structure of the original peptide, either free or bound to a substrate, by NMR spectroscopy, crystallography and/or computer-aided molecular modelling. These techniques aid in the development of novel compositions of higher potency and/or greater bioavailability and/or greater stability than the original peptide (Dean (1994), BioEssays, 16: 683-687; Cohen and Shatzmiller (1993), J. Mol. Graph., 11: 166-173; Wiley and Rich (1993), Med. Res. Rev., 13: 327-384; Moore (1994), Trends Pharmacol. Sci., 15: 124-129; Hruby (1993), Biopolymers, 33: 1073-1082; Bugg et al. (1993), Sci. Am., 269: 92-98, all incorporated herein by reference]. Once a potential peptidomimetic compound is identified, it may be synthesized and assayed using the method described herein to assess its activity. Thus, through use of the methods described above, the present invention provides compounds exhibiting enhanced therapeutic activity in comparison to the peptides described above. The peptidomimetic compounds obtained by the above methods, having the biological activity of the above named peptides and similar three-dimensional structure, are encompassed by this invention. It will be readily apparent to one skilled in the art that a peptidomimetic can be generated from any of the peptides described herein or from a peptide bearing more than one of the modifications described from the previous section. It will furthermore be apparent that the peptidomimetics of this invention can be further used for the development of even more potent non-peptidic compounds, in addition to their utility as therapeutic compounds.

'Inflammation' as used herein means, the local reaction to injury of living tissues, especially the local reaction of the small blood vessels, their contents, and their associated structures. The passage of blood constituents through the vessel walls (extravasation) into the tissues is the hallmark of inflammation. Generally, inflammation starts with an enhanced leukocyte adhesion to the endothelial wall and results in leukocyte extravasation into tissues or organs. In fact, any noxious process that damages living tissue-infection with bacteria, excessive heat, cold, mechanical injury such as crushing, acids, alkalis, irradiation, or infection with viruses can cause inflammation irrespective of the organ or tissue involved. It should be clear that diseases of animals and man classed as 'inflammatory diseases' comprising arthritis, skin inflammation, peritonitis, injury associated with ischaemia/reperfusion (eg. heart, liver, kidney, brain), inflammatory pulmonary disorders (including for example, asthma, bronchitis, adult respiratory distress syndrome (ARDS)), vasculitis, atherosclerosis, nephritis, skin wound healing, sepsis, and local and systemic infections.

By the word 'leukocytes' it is meant white blood cells comprising basophils, neutrophils, eosinophils, granulocytes, monocytes, macrophages and the like. Since the lungs of TM$^{Led/Led}$ mice accumulated significantly. more leukocytes, following LPS inhalation, than those of wild-type mice, we considered the possibility that lack of the N-terminal domain may directly affect leukocyte trafficking. Over 95% of these cells were determined to be neutrophils, with the remainder being monocytes/macrophages. TM is not restricted to vascular endothelial cells, but is also expressed by PMNs and monocytes[66,67]. Indeed, both of these cell sources are unique in that PMN-derived TM is largely intracellular and has not been recovered in an active form, likely due to oxidation of a critical methionine, while monocytes are resistant to TNFα with respect to downregulation of TM expression[68]. Using an in vitro flow chamber model, bone marrow derived PMNs from either TM$^{Led/Led}$ mice or their wild-type counterparts, exhibited similar patterns of rolling, speed and adhesion to a cloned vascular endothelial cell line, indicating that any alteration in PMN trafficking was not likely due primarily to the mutation in TM expressed by the PMN. In contrast, however, PMNs and lymphocytes from either source of mice exhibited increased adhesion to vascular endothelial cells derived from those mice lacking the N-terminal domain. Over 90% of PMN adhesion could be suppressed by addition of a combination of neutralizing anti-P-selectin and anti-ICAM-1 antibodies, indicating that the earliest events in adhesion were intact. However, both baseline and TNFα-induced expression of ICAM-1 was signficantly higher in the TM$^{Led/Led}$ endothelial cells, as was ICAM-1 mRNA accumulation in these mice. VCAM-1 was similarly upregulated in the TM$^{Led/Led}$ mice. Although these findings may be the most relevant explanation for the augmented PMN adhesion and extravasation in the TM$^{Led/Led}$ mice, total suppression of PMN adhesion could not be attained when using combinations of anti-ICAM-1 antibodies, suggesting that other adhesion molecules are likely contributing to the process.

Therefore in yet another embodiment the polypeptides of the present invention can be used to prevent and/or to treat leukocyte adhesion followed by leukocyte extravasation. In yet another embodiment the polypeptides of the present invention the molecules of the present invention can be used to specifically prevent neutrophil extravasation.

In myocardial ischemia/reperfusion studies, infarct sizes, relative to area at risk and left ventricle size, were significantly larger (p<0.005) in the TM$^{LeD/LeD}$ mice, a finding that correlated with extravasafton of polymorphonuclear cells (PMNs) into the damaged myocardial tissue. Thus, in spite of the importance of reperfusion following myocardial ischemia, influx of activated neutrophils results in tissue injury. It is known in the art that the coagulation system has a direct impact on leukocyte infiltration and myocardial damage following ischemia/reperfusion, as inhibition of either tissue factor or thrombin will reduce the region of necrosis and inflammation[75]. The role of TM in MI/R has not been previously directly evaluated, but TM has been implicated in altering the risk of coronary heart disease in humans. The finding of the present invention that a significant increase in infarct size in the TM$^{Led/Led}$ mice in response to MI/R, supports a direct cardioprotective role for the N-terminal lectin-like domain, most likely on the basis of interfering with PMN extravasation into the tissue.

Ischaemia-reperfusion injury is thought to involve a multicomponent process with a burst of free radical production occurring following reperfusion and a second event, inflammatory damage, occurring in a second stage. Ischaemia-reperfusion injury can occur in a variety of tissues, comprising the heart, lung, kidney, gastrointestinal tract, brain and inflammatory joint disease such as rheumatoid arthritis (Korthius and Granger, 1986, in 'Physiology of Oxygen Radicals' Eds. Taylor, Matalos and Ward; Allen et al., 1989, Lancet ii, 282-283). Treatment of ischaemia/reperfusion-induced injury requires the development of compounds which suppress the harmful effects of oxygen radicals during both the reperfusion and inflammatory phases. Due to the multifactorial nature of ischaemia-induced injury, it has been a problem to find compounds which can be used for treatment. In a particular embodiment the polypeptides of the present invention can be used to treat and/or to prevent inflammation which occurs as a result of ischaemia-reperfusion injury.

The term 'medicament to treat' relates to a composition comprising polypeptides as described above and a pharmaceutically acceptable carrier or excipient (both terms can be used interchangeably) to treat diseases as described herein. The administration of a polypeptide as described above or a pharmaceutically acceptable salt thereof may be by way of oral, inhaled or parenteral administration. The active compound may be administered alone or preferably formulated as a pharmaceutical composition. An amount effective to treat inflammatory disorders described herein depends on the usual factors such as the nature and severity of the disorders being treated and the weight of the mammal. However, a unit dose will normally contain 0.01 to 50 mg for example 0.01 to 10 mg, or 0.05 to 2 mg of the lectin-like fragment of thrombomodulin (or a fragment or homologue thereof) or a pharmaceutically acceptable salt thereof. Unit doses will normally be administered once or more than once a day, for example 2, 3, or 4 times a day, more usually 1 to 3 times a day, such that the total daily dose is normally in the range of 0.0001 to 1 mg/kg; thus a suitable total daily dose for a 70 kg adult is 0.01 to 50 mg, for example 0.01 to 10 mg or more usually 0.05 to 10 mg. It is greatly preferred that the compound or a pharmaceutically acceptable salt thereof is administered in the form of a unit-dose composition, such as a unit dose oral, parenteral, or inhaled composition. Such compositions are prepared by admixture and are suitably adapted for oral, inhaled or parenteral administration, and as such may be in the form of tablets, capsules, oral liquid preparations, powders, granules, lozenges, reconstitutable powders, injectable and infusable solutions or suspensions or suppositories or aerosols. Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well-known methods in the art. Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate. These solid oral compositions may be prepared by conventional methods of blending, filling, tabletting or the like. Repeated blending operations may be used to distribute the active agent throughout those compositions employing large quantities of fillers. Such operations are, of course, conventional in the art. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin,. sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents. Oral formulations also include conventional sustained release formulations, such as tablets or granules having an enteric coating. Preferably, compositions for inhalation are presented for administration to the respiratory tract as a snuff or an aerosol or solution for a nebulizer, or as a microfine powder for insufflation, alone or in combination with an inert carrier such as lactose. In such a case the particles of active compound suitably have diameters of less than 50 microns, preferably less than 10 microns, for example between 1 and 5 microns, such as between 2 and 5 microns. A favored inhaled dose will be in the range of 0.05 to 2 mg, for example 0.05 to 0.5 mg, 0.1 to 1 mg or 0.5 to 2 mg. For parenteral administration, fluid unit dose forms are prepared containing a compound of the present invention and a sterile vehicle. The active compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum. Parenteral suspensions are prepared in substantially the same manner except that the compound is suspended in the vehicle instead of being dissolved and sterilised by exposure to ethylene oxide before suspending in the sterile vehicle. Advantageously, a surfactant or wefting agent is included in the composition to facilitate uniform distribution of the active compound. Where appropriate, small amounts of bronchodilators for example sympathomimetic amines such as, isoprenaline, isoetharine, salbutamol, phenylephrine and ephedrine; xanthine derivatives such as theophylline and aminophylline and corticosteroids such as prednisolone and adrenal stimulants such as ACTH may be included. As is common practice, the compositions will usually be accompanied by written or printed directions for use in the medical treatment concerned.

The present invention further provides a pharmaceutical composition for use in the treatment and/or prophylaxis of herein described disorders which comprises a polypeptide or a pharmaceutically acceptable salt thereof, or a pharmaceutically acceptable solvate thereof, and, if required, a pharmaceutically acceptable carrier thereof.

Another aspect of administration for treatment is the use of gene therapy to deliver the above-mentioned functional polypeptides. Gene therapy means the treatment by the delivery of therapeutic nucleic acids to patient's cells. This is extensively reviewed in Lever and Goodfellow 1995; Br. Med Bull.51, 1-242; Culver 1995; Ledley, F. D. 1995. Hum. Gene Ther. 6, 1129. To achieve gene therapy there must be a method of delivering genes to the patient's cells and additional methods to ensure the effective production of any therapeutic genes. There are two general approaches to achieve gene delivery; these are non-viral delivery and virus-mediated gene delivery. As a non-limiting example a recombinant adenoviral vector can be generated comprising a functional fragment or homologue of SEQ ID NO: 1, 2, 3, 4, 5, 6, 7 or 8.

In another embodiment of the invention a polypeptide to prevent and/or to treat inflammation as described above, can be used in combination with molecules known in the art to prevent and/or to treat inflammation.

According to still further features in the described preferred embodiments provided is a recombinant vector comprising a polynucleotide sequence encoding a functional polypeptide as described above. A 'functional polypeptide' is a polypeptide or homologue derived from SEQ ID NO:1 capable of suppressing inflammation. The vector may be of any suitable type including, but not limited to, a phage, virus, plasmid, phagemid, cosmid, bacmid or even an artificial chromosome. The polynucleotide sequence encoding a polypeptide capable of suppressing inflammation may include any of the above described polypeptide fragments. The term 'recombinant DNA vector' as used herein refers to DNA sequences comprising a desired coding sequence and appropriate DNA sequences necessary for the expression of the operably linked coding sequence in a particular host organism (e.g. a mammal). DNA sequences necessary for expression in prokaryotes include a promoter, optionally an operator sequence, a ribosome-binding site and possibly other sequences; Eukaryotic cells are known to utilize promoters, polyadenylation signals and enhancers.

According to still further features in the described preferred embodiments provided is a host cell which comprises an exogenous polynucleotide fragment including a polynucleotide sequence encoding a polypeptide as described above having the possibility to suppress inflammation.

The exogenous polynucleotide fragment may be any of the above-described fragments. The host cell may be of any type such as prokaryotic cell, eukaryotic cell, a cell line, or a cell as a portion of a multicellular organism (e.g., cells of a transgenic organism).

In another embodiment the invention provides a process for producing the recombinant polypeptides. Said process comprises the following steps: (1) preparing a DNA fragment comprising a nucleotide sequence which encodes said polypeptide, (2) incorporating said DNA fragment into a recombinant DNA vector which contains said DNA fragment and is capable of undergoing replication, (3) transforming a host cell with said recombinant DNA fragment to isolate a transformant which can express said polypeptide, and (4) culturing said transformant to allow the transformant to produce said polypeptide and recovering said polypeptide form resulting cultured mixture.

According to still further features in the described preferred embodiments provided is a recombinant protein including a polypeptide as described above capable of suppressing inflammation. The recombinant protein may be purified by any conventional protein purification procedure close to homogeneity and/or be mixed with additives. The recombinant protein may be manufactured using recombinant expression systems comprising bacterial cells, yeast cells, animal cells, insect cells, plant cells or transgenic animals or plants.

EXAMPLES

1. Deletion of the Lectin Domain of TM and Expression in COS Cells

The role of the lectin-like domain of murine TM was evaluated by deleting the entire domain using recombinant PCR, while retaining the putative signal peptide. COS cells were transfected with murine TM cDNA encoding both wild-type and mutated TM. Northern analysis of RNA derived from the TM-expressing cells and control cells transfected with the expression vector (pcDNA3.1) alone, confirmed the specificity and expected TM mRNA processing. Indirect immunofluorescence using specific rabbit anti-TM antibodies revealed that wild-type and the mutated TM could be transported through the cell for stable cell surface expression. Thrombin-dependent activation of protein C was specifically and similarly augmented on the surface of COS cells expressing either wild-type or the mutated TM. Using an equal number of confluent cells, the rate of change in absorbance of the chromogenic substrate S2238 at 405 nm was used to determine TM-cofactor function in thrombin-dependent activation of protein C. In vector-alone transfected COS cells, the rate of change in absorbance was 0.01 units/min, whereas it was $0.21 \pm 0.04$ (n=3) units/min and $0.23 \pm 0.04$ (n=3) units/min for those cells transfected with wild-type or mutated TM, respectively, indicating that both forms of TM are similarly functional with respect to protein C activation.

2. Generation of Mice Lacking the Lectin Domain of TM

A targeting vector was constructed in which the wild-type coding region of the murine TM gene was replaced with one that encoded TM that lacks the N-terminal amino acid residues between the putative signal peptide and the first EGF-like repeat, yet retained the neomycin selection marker gene in the 3'-untranslated region (UTR) of the gene. Following electroporation of R1 ES cells, over 350 clones were picked, 4 of which were determined to have homologously recombined the replacement vector in a single copy, as evaluated by Southern blotting. PCR and DNA sequencing were used to confirm that the entire coding region of the mutated allele with the appropriate deletion was intact. Two of the positive ES cell clones were expanded and aggregated for generation of chimeric mice, two of which transmitted to germline.

3. Viability of Gene-targeted Mice

Cross-breeding of F1, $TM^{LeDneo/wt}$ mice (with 1 wild-type allele and 1 mutant allele, the latter with the neomycin gene in the 3'-UTR) resulted in over 250 offspring. Genotyping of tail DNA was performed by PCR analysis, and occasionally confirmed by Southern blotting. The genotypes of F2 progeny were distributed in a Mendelian inheritance pattern of 26.1% ($TM^{wt/wt}$), 48.7% ($TM^{LeDneo/wt}$) and 25.2% ($TM^{LeDneo/LeDneo}$) at birth indicating that intrauterine death was not occurring. There was an equal distribution of male and female births, and there were no apparent differences in weight, growth, development or fertility up to 18 months of age. We considered the possibility that the neomycin gene within the 3'UTR might affect regulation of the mutated TM, and for this reason excised it by cross-breeding $TM^{LeDneo/wt}$ mice with mice ubiquitously expressing Cre recombinase under the control of the PGK promoters (strategy in FIG. 2)., Excision of the loxP-flanked neomycin gene was confirmed by PCR of genomic DNA and by RT-PCR of RNA derived from several tissues derived from the offspring. The resultant $TM^{LeD/wt}$ mice (with 1 wild-type allele and 1 mutant allele, the latter lacking the neomycin gene) were intercrossed and the genotypes of F2 progeny (over 300) were also distributed in a Mendelian inheritance pattern, again indicating that deletion of the N-terminal lectin-like domain did not cause embryonic lethality. The reported results are not likely to reflect a strain-specific artefact, since in limited studies, back-crossing onto 129sv/se and C57/Bl6 backgrounds resulted in similar phenotypes.

4. Expression of TM by $TM^{wt/wt}$ and $TM^{LeD/LeD}$ Mice

Deletion of the lectin-like domain of TM in vivo did not affect cellular distribution of the molecule during development. Immunoperoxidase staining of sagittal sections of 11.5 to 14.5 dpc embryos revealed TM in all tissues. The total amount of TM in lung tissue was indirectly quantitated using a radioimmunoassay. When comparing $TM^{LeD/LeD}$ mice with their wild-type counterparts, there was no difference in lung TM antigen levels (p<0.01), whereas TM antigen levels in the $TM^{LeDneo/LeDneo}$ mice were suppressed to approximately 20% of those in the wild-type and $TM^{LeD/LeD}$ mice.

5. Thrombogenic Stresses

Hypoxia for 16-18 hours results in the deposition of fibrin and platelet thrombi within the lung vasculature, with thrombogenicity augmented in mice heterozygous for the TM gene[17], and in mice expressing TM that has markedly reduced protein C cofactor activity[16]. Baseline levels of lung tissue fibrin[16], and plasma FPA[24] were similar in the TM$^{wt/wt}$ and TM$^{LeD/LeD}$ mice (Table 1). Exposure to hypoxia did not significantly affect either of these markers (p>0.1). The efficacy of the model was substantiated by the observation that 7 of 18 TM$^{LeDneo/LeDneo}$ mice (with ~20% TM antigen levels) died during the hypoxic stress with postmortem evidence of massive pulmonary thrombosis, while no TM$^{LeD/LeD}$ mice and only 1 TM$^{wt/wt}$ mouse died. Overall, the results of these experiments suggest that (1) suppression of TM expression to levels below 20% predispose the mice to fibrin deposition under this particular stress, (2) the N-terminal lectin-like domain of TM has no role in altering the coagulation system in response to hypoxia, and (3) the integrity of the EGF-like domains of TM known to be involved in coagulation, has not been signficantly altered by deletion of the N-terminal domain in the TM$^{LeD/LeD}$ mice.

6. Inflammatory Stresses

To evaluate the response to endotoxin, lethal doses of LPS (40 μg/gm of body weight) were administered to TM$^{LeD/LeD}$ and TM mice (n=22 for each group). Over 50% of TM$^{LeD/LeD}$ mice died within the first 26 hours following exposure to the LPS, while in the same period, less than 10% of the wild-type mice had died. LPS 20 μg/gm was also administered i.p. to mice of each genotype, and 6 hours later, they were sacrificed and examined for fibrin deposition in histologically sectioned lungs, brain and kidney, using methods as previously reported[24]. As compared with their wild-type counterparts, we could not detect an alteration in deposition of fibrin in the tissues of TM$^{LeD/LeD}$ mice in response to the LPS (Table 2). Levels of TNFα, IL-1β, and IL-10 were measured in plasma obtained 6 hours following i.p. injection of LPS 20 μg/gm (Table 3). Baseline levels of these cytokines were undetectable in all the groups of mice. Notably, however, plasma levels of TNFα and IL-1β were significantly elevated in those mice lacking the lectin domain (p<0.05, n=18), while IL-10 and IL-6 levels were unaffected by the mutation in TM. The absolute level of TM antigen did not appear to affect this response, i.e. there was no significant difference in cytokine response between the TM$^{LeD/LeD}$ and the TM$^{LeDneo/LeDneo}$ mice (p>0.5). Although peripheral white blood cell and absolute circulating neutrophil counts appeared to be somewhat higher in the mutant mice following LPS exposure, these differences were not statistically significant (p>0.1). In those mice lacking the lectin-like domain (TM$^{LeD/LeD}$), hematoxylin and eosin, and myeloperoxidase stains of lung tissue sections obtained before the sublethal LPS stress suggested that there was a moderate increase in accumulation of neutrophils and/or macrophages in the interstitium of the lungs. Staining of the lung sections with monocyte/macrophage-specific Mac3 antibody confirmed that over 95% of the myeloperoxidase-stained cells were neutrophils. These cells were widely distributed throughout the interstitium, in peri-bronchial locations and occasionally in the alveolar spaces. Lung sections from mice with both diminished levels of TM antigen and the mutation were similarly infiltrated with neutrophils, as compared with wild-type mice—but not more than in the TM$^{LeD/LeD}$ mice. Lung architecture in both the mutant and wild-type mice was not signficantly altered. There was no evidence of chronic inflammation or of bronchial epithelial hyperplasia, nor were there abnormalities in the blood vessels, findings consistent with the mild degree of leukocyte infiltration. Due to the inherent difficulties in quantifying irregularly distributed cells on these lung sections, we chose to more closely evaluate the response of the mice to a local inflammatory stimulus. TM and TM$^{LeD/LeD}$ mice were therefore exposed for 10 minutes to LPS administered via a nebulizer. Three hours after the treatment, bronchoalveolar lavage fluid (BALF) analyses were performed, and myeloperoxidase activity was quantitated (Table 4). Although baseline measurements, were not significantly different between wild-type and TM$^{LeD/LeD}$ mice, LPS inhalation induced ~3.5-fold increase in BALF myeloperoxidase activity in the mutant mice (p<0.005), whereas absolute neutrophil counts in the BALF from TM$^{LeD/LeD}$ mice increased approximately 2-fold. Similar to our findings with i.p. administration of LPS, circulating levels of neutrophils increased in response to inhaled LPS, but not to a significant degree under these experimental conditions. Ultrastructural evaluation of the lungs revealed evidence of accumulation of neutrophils particularly in peribronchial sites, consistent with local LPS exposure, in addition to some interstitial accumulation beyond the vessels. No evidence of overt lung damage was otherwise noted. Overall, these studies are supportive of an in vivo role for the N-terminal domain of TM in regulating neutrophil extravasation.

7. Activation of Protein C by Endothelial Cells of Mice

Since APC has direct anti-inflammatory properties, alterations in functional expression of TM might result in diminished activation of protein C and loss of its anti-inflammatory effect, leading to augmentation in neutrophil activation and adhesion/migration as well as a more prominent cytokine response. In view of our observation that the cytokine response in those mice lacking the N-terminal lectin domain was more pronounced than in wild-type mice, we sought to further confirm that cell surface expression of TM was not affected by deletion of the N-terminal lectin-like domain. We directly quantitated functional expression of TM on the blood vessel wall in vivo, by administering human protein C intravenously, and measuring the generation of APC. As seen in Table 5, 15 minutes after infusion of 100 μg of purified human protein C into TM$^{wt/wt}$, TM$^{LeD/LeD}$ and TM$^{LeDneo/LeDneo}$ mice, plasma concentrations of both the unactivated and activated forms of protein C were not significantly altered. The absence of an effect on protein C activation in the TM$^{LeDneo/LeDneo}$ mice that have ~20% TM antigen levels, is not surprising since much lower TM levels are likely required to result in alterations, particularly without stress. For each genotype, mice were also exposed to LPS 10 μg/g, 4 hours after which human protein C was infused as above. Once again, generation of activated protein C was similar in all groups, although APC levels were significantly higher when comparing the mice exposed to LPS to those unexposed mice with the same genotype (p<0.05). Overall, however, these studies confirm that TM function in vivo, with respect to activation of protein C, is not significantly diminished in those mice lacking the N-terminal lectin-like domain. Due to the importance of excluding the possibility that TM cell surface expression is diminished in the TM$^{LeD/LeD}$ mice, we also derived endothelial cells from TM$^{LeD/LeD}$ mice and their wild-type counterparts for evaluation of their ability to support thrombin-dependent protein C activation. This was done in two ways. In the first, cultured lymphatic endothelial cells were derived from adjuvant-induced intraperitoneal lymphangiomas[34]. This method facilitates the derivation of highly purified populations of endothelial cells, characterized by expression of Flk-1 and Flt4 as lymphatic in origin, directly from transgenic mice. From each genotype, we evaluated mRNA levels and cell-surface functional expression of TM. TM mRNA accumulation in the lymphatic endothelial cells derived from wild-type and $TM^{LeD/LeD}$ mice was similar, while cell-surface thrombin-dependent activation of protein C was also not significantly different in several different clones. We also generated several transformed endothelial cell lines from intraperitoneal vascular tumors induced to grow in the mice following injection of retrovirus carrying the middle T antigen of murine polyomavirus (PymT)[32,33], and those cells from the wild-type and $TM^{LeD/LeD}$ mice expressed similar quantities of TM, as assessed by Northern blots and cell-surface activation of protein C. Overall, our data support the conclusion that changes in activation of protein C are not the primary mechanism altering the inflammatory response in $TM^{LeD/LeD}$ mice.

8. Adhesion of Leukocytes to Endothelial Cells

Since TM expression is not restricted to vascular endothelial cells, but is also synthesized by other cells including neutrophils and monocytes, we considered the possibility that the increase in leukocyte efflux into the lungs might be a result of TM alterations on either the neutrophils and/or the vascular endothelium. fEND.5 cells are an established PymT transformed murine endothelial cell line that expresses full-length, functional TM on the cell surface. In a flow chamber model, adhesion and rolling of neutrophils (PMNs) derived from the bone marrows of $TM^{wt/wt}$ and $TM^{LeD/LeD}$ mice to unperturbed and TNFα-treated fEND.5 cells was determined to be unaltered by the presence or absence of the N-terminal lectin-like domain of TM in neutrophils (Table 6), evidence that the primary defect does not involve the PMNs. Adhesion and rolling of neutrophils to transformed endothelial cells derived from the $TM^{wt/wt}$ and $TM^{LeD/LeD}$ mice were consequently evaluated. As can be seen in Table 7, TNFα stimulation of endothelial cells from either source of mice significantly enhanced adhesion of neutrophils, similarly to the experiments with the fEND.5 cells. Adhesion of neutrophils from mice of either genotype to TNFα-stimulated endothelial cells derived from $TM^{LeD/LeD}$ mice was significantly augmented, as compared to adhesion to endothelial cells from wild-type counterparts. This was determined not to be an endothelial cell clone-specific artifact, as 3 different clones of endothelial cells were evaluated with similar results. There was also a significant 3-fold increase in PMN and lymphocyte adhesion to resting $TM^{LeD/LeD}$ endothelial cells as compared to $TM^{wt/wt}$ endothelial cells (Table 8). The effects were similar, irrespective of the source of leukocytes, i.e. whether the leukocytes were derived from the bone marrows of $TM^{LeD/LeD}$ or wild-type mice. Addition of polyclonal anti-TM antisera (that identifies regions both within and outside the N-terminal region of TM) to the $TM^{wt/wt}$ endothelial cells resulted in enhanced PMN adhesion (p<0.005), while pre-immune sera had no effect. Furthermore, adhesion of PMNs to $TM^{LeD/LeD}$ endothelial cells was not affected by the anti-TM antisera, these data suggesting that the N-terminal domain of TM is indeed mediating the enhanced leukocyte adhesion. Finally, the unlikely possibility that thrombin might be affecting adhesion in the assays was excluded by the finding that the addition of PPACK had no effect on the results. To evaluate the mechanism by which adhesion of PMNs to the endothelial cells of $TM^{LeD/LeD}$ mice is enhanced, we attempted to abrogate adhesion in the flow model by using blocking anti-ICAM-1 antibodies. In resting wild-type endothelial cells, where adhesion was minimal, there was a slight non-significant decrease in adhesion of neutrophils. Anti-ICAM-1 antibodies interfered with over 75-80% of adhesion of neutrophils to wild-type, endothelial cells that were stimulated with TNFα. In contrast, neutrophil adhesion to resting $TM^{LeD/LeD}$ endothelial cells was suppressed by about 50% with anti-ICAM-1 antibodies. Treatment with TNFα further augmented adhesion, and again, the anti-ICAM-1 antibody was only partially effective at blocking adhesion, causing a decrease of only approximately 30%. PMN adhesion to TNFα-treated endothelial cells from either $TM^{LeD/LeD}$ or wild-type mice was suppressed by over 90% when both anti-ICAM-1 and anti-P-selectin antibodies were added. The results suggest that 1. the $TM^{LeD/LeD}$ endothelial cells have enhanced surface expression of functional ICAM-1, and 2. that other pathways are active in augmenting the adhesion of PMNs to these endothelial cells.

9. Effects of Recombinant Soluble Lectin-like Domain of TM on Leukocyte Adhesion and Cytokine Response Constitutive levels of circulating soluble TM, composed of proteolytic components of the extracellular domains, are found in the plasma of normal individuals, while quantitative changes occur in different disease states. Purified recombinant $TM_{lec155}$ was prepared using the *Pichia pastoris* expression system, and further purified by a series of chromatographic steps as detailed in the methods. In a static adhesion assay on $TM^{Led/Led}$ endothelial cells, PMNs were co-incubated with $TM_{lec155}$ at two concentrations. Adhesion of PMNs to the resting endothelial cells was, as before, increased as compared with adhesion to wild-type endothelial cells (Table 9). Addition of recombinant $TM_{lec155}$ resulted in a significant decrease in adhesion (p<0.001), with an apparent dose response. The degree of suppression of adhesion was almost to the level of adhesion to wild-type endothelial cells. Adhesion of PMNs to TNFα-activated $TM^{Led/Led}$ endothelial cells was also significantly reduced by recombinant $TM_{lec155}$ (p<0.001), but not to the level of resting endothelial cells. The role of recombinant $TM_{lec155}$ in vivo was tested by injecting wild-type mice with LPS 20 µg/gm i.p., followed 5 minutes later with an intravenous bolus of recombinant $TM_{lec155}$ or buffer alone. After a further 3 hours, the serum cytokine response was determined. As seen in Table 10, IL-1β levels were significantly suppressed by administration of the recombinant $TM_{lec155}$, as compared with the control (p=0.02).

10. Effects of Recombinant Human TM Fragments on Leukocyte Adhesion

In order to evaluate the function of the lectin-like domain of human TM, fragments 1, 2 and 4 (SEQ ID NO. 1, 2, 4 respectively) representing amino acid ranges 1 to 224, 1 to 157, and 33 to 159 of the mature protein, respectively, were expressed by the *Pichia pastoris* system. The recombinant protein was purified either through a series of column chromatography steps including phenyl-sepharose, Q-sepharose, and size-fractionation, and/or by affinity chromatography using immobilized murine anti-murine $TM_{lec155}$ monoclonal antibodies that were raised in $TM^{LeD/LeD}$ mice, and demonstrated to cross-react with the lectin-like domain of TM derived from mice or humans. The purified fragments were demonstrated to be homogeneous by SDS-PAGE and Western immunoblotting, appearing at the appropriate apparent molecular weight as monomers or dimers, and occasionally as multimers.

Static adhesion assays using human neutrophils (50,000 per well) and confluent fEND.5 cells in 24-well plates were performed exactly as described (see below—Methods section 11). Where noted, TNFα (200 U/ml) or LPS 20 µg/ml, were used to activate the fEND.5 cells for 3 hrs. PMNs were co-incubated with one of the recombinant human TM fragments 1, 2 or 4, (SEQ ID NO 1, 2, 4) or with HPLC-purified peptides representing human TM fragments 3,6 or 7 (SEQ ID NO 3, 6, 7). Tables 11-17 show results, where the amount of recombinant fragment in μg is shown on the bar graphs, and * indicates p<0.05 as compared with buffer control (i.e. without recombinant protein) under the same conditions. In all cases, appropriate controls were used for comparisons.

Fragment 1 (SEQ ID NO 1) comprising the entire N-terminal domain of human TM (amino acids 1 to 226 of the mature protein) significantly suppressed LPS and TNF-induced adhesion of human neutrophils to fEND.5 cells (p<0.001) in a dose-responsive manner (Tables 11,12). Similarly, fragment 2 significantly suppressed LPS-induced neutrophil adhesion (p<0.001) (Table 13). Fragment 4 (SEQ ID NO 4) also suppressed neutrophil adhesion induced by LPS and TNF (p<0.05) (Tables 14, 15).

The capacity of the peptides (fragments 3, 6 and 7) (SEQ ID NO 3, 6, 7) have also been evaluated. At the highest concentration tested, fragment 3 (SEQ ID NO 3) significantly suppressed LPS-induced neutrophil adhesion (p<0.001). Human TM fragment 7 (SEQ ID NO 7) appeared to be more potent, and significantly suppressed neutrophil adhesion to the fEND.5 cells (p<0.001) (Table 17).

Overall, the data suggests that several fragments of the lectin-like domain of TM can interfere with adhesion of neutrophils or leukocytes to the vascular endothelium, and thus which can form the basis for anti-inflammatory therapies. These are currently being tested in a variety of in vivo models of inflammation.

11. Activation of $ERK_{1/2}$ is Modulated by the N-terminal Domain of TM

The MAP kinase intracellular signaling pathway is implicated in regulating expression of adhesion molecules. We examined activation of $ERK_{1/2}$ in heart lysates of mice before and after LPS exposure. Total $ERK_{1/2}$ levels remained stable. In mice treated with PBS, baseline levels of phosphorylated $ERK_{1/2}$ were similar between genotypes. After LPS, heart lysates from $TM^{wt/wt}$ mice exhibited little phosphorylation of $ERK_{1/2}$. In contrast, a significant increase in activation of $ERK_{1/2}$ was detected in heart lysates of $TM^{LeD/LeD}$ mice. These data suggest that the lectin-like domain of TM suppresses LPS-induced phosphorylation of $ERK_{1/2}$.

We predicted that soluble lectin-like domain of TM would suppress PMN adhesion by altering regulation of MAP kinase pathways in ECs. Therefore, HUVECs were exposed to TNFα (200 U/ml) for 20 minutes. Accumulation of $pERK_{1/2}$ and NFκB were markedly suppressed, although not totally abrogated, by addition of $GST-TM_{lec155}$, while GST alone had no effect. Total $ERK_{1/2}$ levels remained unchanged. $TM_{lec155}$ similarly interfered with TNFα-induced upregulation of $pERK_{1/2}$ and NFκB expression by HUVECs, suggesting that the lectin-like domain of TM suppresses PMN adhesion to ECs via MAP kinase signaling.

Because endothelial cell death is a pathway of sustained tissue damage, we evaluated whether $TM_{lec155}$ was capable of rescuing HUVECs from serum starvation-induced cell death. After 3 days of serum deprivation, over 95% of HUVECs died. Serum starvation with the addition of $TM_{lec155}$ at concentrations of 1, 10 and 20 μg/ml rescued 2±0.6%, 18±7% and 34±14% of the cells (p=0.69, p<0.05, p<0.05, respectively compared with serum-starved controls), showing that soluble TM rnay also have pro-survival properties.

12. Myocardial Ischemia/Reperfusion

Myocardial schemia/reperfusion (MI/R) injury is characterized by PMN extravasation and cytokine release, with consequent tissue damage. We evaluated the role of the N-terminal lectin-like domain of TM in this process by utilizing a well-established murine model. The LAD coronary arteries of $TM^{Led/Led}$ and $TM^{wt/wt}$ mice were transiently occluded for 30 minutes, followed by 3 hours of reperfusion, after which infarct sizes, LV sizes, and areas at risk (AAR) were measured. Mortality rates during the surgical procedure were similar in both groups. Infarct size in $TM^{Led/Led}$ vs $TM^{wt/wt}$ mice as a function of LV size was 28.8±4.1 (n=10) and 21.7±4.6 (n=11) or as a function of AAR was 47.8±5.2 (n=10) and 35.8±5.8 (n=11), respectively, both measures reflecting a significantly larger necrotic area in the $TM^{Led/Led}$ mice (p<0.002). To confirm that the increase in infarct size in the mutant mice was associated with enhanced PMN extravasation, PMN "homing" assays were performed, in which bone-marrow derived purified and fluorescently labeled PMNs were infused into the coronary artery at the time of reperfusion, and 3 hours later, the number of PMNs were quantitated following histological sectioning. For each experiment, the same source PMNs were used for one wild-type and one $TM^{Led/Led}$ mouse, in alternating order. In 2 independent experiments, the $TM^{Led/Led}:TM^{wt/wt}$ ratio of PMNs in the right ventricle (RV), outside the MR, in the LV, and in the MR was 1.35±0.4, 1.4±0.6, 3.2±0.6, and 4.2±0.6, respectively, indicating that extravasation of PMNs following MI/R in the $TM^{Led/Led}$ is significantly enhanced.

13. Wound-healing

TM expression by suprabasal keratinocytes has been demonstrated to be upregulated both during epidermal differentiation and following injury, particularly at the migrating edge of a healing skin wound[42], although mice with <1% TM levels have been reported to have normal rates of skin wound healing[43]. In $TM^{Led/Led}$ mice, the rate of healing was not significantly different over a 9-day period (Table 11). However, there was a significant delay in healing noted at days 4 and 7 in the $TM^{LeDneo/LeDneo}$ mice (p<0.05), as compared with wild-type mice or mice lacking the cytoplasmic domain of TM. By 9 days following the incision, healing was not different from normal—either in appearance or in size of the remaining wound. Thus, while the absence of the N-terminal lectin-like domain of TM alone does not appear to significantly alter skin wound healing, the lack of this structure in combination with low antigenic levels of TM (<20%), does have at least a transient effect on wound healing.

14. The Generation of a Recombinant Adenoviral Vector

The cDNA encoding various fragments of the lectin-like domain of TM (e.g. nucleotide sequences encoding for example polypeptide SEQ ID NO: 1, 2, 3, 4, 5, 6, 7 or 6 or a nucleotide sequence encoding the murine TMlec223) is cloned between the strong enhancer/promoter of the cytomegalovirus (CMV) immediate early genes and the SV40 polyadenylation signal of the bacterial plasmid pACCMV-pLpA (Gomez-Foix A. et al. (1992) *J. Biol. Chem.* 267, 25129 and Janssens S. P. et al. (1996) *J. Clin. Invest.* 98(2)317). In some constructs, a fusion cDNA is inserted so that a TM-lacZ protein is generated, such that localization of administered TM can be monitored. The plasmid also contains E1A-deleted sequences of type 5 adenovirus including the origin of replication and the packaging signal and a polylinker. Recombinant adenovirus is generated through homologous recombination with pJM17, a bacterial plasmid containing the full-length adenoviral genome, following cotransfection in E1A-transformed human embryonic kidney (293) cells. The presence of TM cDNA in virion DNA isolated from infected 293 cells is confirmed by PCR analysis. TM-containing viral isolates (AdCMV.TM) is amplified on confluent 293 cells and, after appearance of cytopathic effects, isolated, precipitated, and concentrated by discontinuous CsCl gradient. Viral titers are determined by infection of monolayers of 293 cells with serial dilutions of the recombinant adenovirus. For in vivo studies, viral titers are adjusted to $5 \times 10^9$ plaque forming units (pfu)/ml. The response of the recombinant adenoviruses is monitored in 2 in vivo models. In both cases, we anticipate that administration of the lectin-like domain of TM diminishes extravasation of leukocytes into the tissue, decrease inflammation and decrease injury. Model 1: mice with myocardial ischemia/reperfusion injury. Using the model as described herein, mice are pre-treated with AdCMV.TM or control AdCMV at increasing doses as quantitated by pfu/ml. Doses start at ~$10^7$ pfu and escalate depending on response. Treatment is administered intravenously 3 days prior to MI/R. Infarct sizes as a function of area at risk are measured. Expression of AdCMV.TM in the heart is evaluated by RT-PCR. In alternative approaches, a cardiac specific promoter, such as that for the myosin-heavy chain, may be used in construction of the adenovirus, such that localized expression of the lectin-like domain may be ensured. Furthermore, regulated expression as being developed by other groups, may facilitate expression of TM fectin-like domain in the heart, such that enhanced TM expression may be provided during periods of ischemia/reperfusion, thus preventing leukocyte extravasation and preventing further injury. Model 2: mice with antgen-induced arthritis (Rabinovich, G A et al. (1999) *J. Exp. Med.* 190, 385) is evaluated for their response to administration of AdCMV.TM. In this case, prior to or shortly after exposing the mice to the antigen, a single dose of AdCMV.TM or controls, is given to the mice (starting at $10^7$ pfu) either intraperitoneally, intravenously or intra-articularly. At the time points that arthritis is generally maximal in control mice, and otherwise at regular intervals, joints are evaluated clinically and histologically for changes in inflammation, i.e. synovial fluid cellular infiltration and cytokine levels, chrondrocartilage damage and proliferation and intra-articular vascular growth (pannus).

15. In Vivo Effect of Recombinant Lectin-like Domain

In a mouse myocardial ischemia/reperfusion model, one hour prior to the time of reperfusion, we administer escalating doses (o μg, 1 μg, 5 μg, 10 μg and 50 μg) of recombinant thrombomodulin lectin-like domain, or fragments or homologues thereof (designated as Tmlec), intravenously. Following 30 minutes of ischemia of the LAD coronary artery, reperfusion is be initiated at which point a second dose of TMlec (escalated with subsequent experiments depending on response) is be administered directly into the LAD coronary artery. After 3 hours, the mice hearts are evaluated for infarct size relative to area at risk, and leukocyte extravasation into different parts of the heart, i.e. inside and outside of the infarct zone. Control studies without TMlec administration is performed. Both wild-type and $TM^{Led/Led}$ mice are used for these studies. Myocardial function is also monitored. We expect that treatment with appropriate doses of TMlec is cardioprotective and decrease leukocyte extravasation into the myocardial tissue. Furthermore, no side effects from this treatment are anticipated.

Materials and Methods

1. Isolation of the Murine Thrombomodulin Gene

The murine TM gene, derived from a murine 129Sv genomic PAC library (Genome Systems, IN), and containing an intracisternal A-particle (IAP) provirus in the 5' untranslated region (5'-UTR)[23], was isolated as previously reported[24]. A 12 kb Kpn1 fragment, containing the entire coding region, was subcloned into pBS (Stratagene Inc., Mississauga, Canada), resulting in Kpn12/BS.

2. Construction of a Targeting Vector to Delete the N-terminal Lectin-like Domain of TM In order to replace the wild-type coding region of TM with one that encodes TM lacking the lectin-like domain, PCR-based mutagenesis with oligonucleotides containing overlapping complementary regions TM.s1957i (sense 5'-GGGCTCTCCGCACTATGCAGCGTGGAGAATGGT-GGCTGT), and TM.as287i (antisense 5'-ATTCTCCACGC-TGCATAGTGCGGAGAGCCCCAGGCTAGC), was used. Two polymerase chain reactions were performed. In the first, oligonucleotide primer TMs-240 (sense 5'-TTCTGTGGTG-GCGCCTGCAGGCCACGCCCG) was paired with antisense primer TMas287i, resulting in a 541 bp fragment. In the second, sense oligonucleotide primer TM.s1957i was paired with antisense primer TM.as2613EO (5'-TGGAC-TAGTTMTTMGATCTTCCTCGAGGCGCGCCGTTCA-GCTGAAATATT TTAGC), yielding a 1633 bp fragment. These products were purified and used for recombinant PCR with oligonucleotide primers TM.s-240 and TM.as2613EO. The recombined 2206 bp amplicon was subcloned into the TA-cloning vector pCR2.1 (Invitrogen, CA), and DNA sequencing confirmed the presence of the desired deletion. This DNA fragment extends from a Nar1 restriction enzyme site 230 bp upstream of the transcriptional start site, through the coding region of the gene, and 643 bp into the 3' untranslated region (3'-UTR). Oligonucleotide primer TM.as2613EO resulted in the addition of Asc1, Xho1, BglII, Pac1 and Spe1 restriction sites at the 3' end of the recombined product, to be used for subcloning and ES cell DNA screening. The final translated protein product represents the intact TM protein, retaining the putative 20 amino-acid residue signal peptide, and lacking the subsequent $NH_2$-terminal 223 amino acid residues of the lectin-like domain ($NH_2$-AKLQPTGSQCVEHECFALFQGPATFLDASQAC-QRLQGHLMTVRSSVAADVISLLLSQSSMDLGPWIGL-QLPQGCDDPVHLGPLRGFQWVTGDNHTSYSRWAR-PNDQTAPLCGPLCVTVSTATEMPGEPAWEEKPCETE-TQGFLCEFYFTASCRPLT VNTRDPEAAHISSTYNTPF-GVSGADFQTLPVGSSAAVEPLGLELVCRAPPGTSEG-HWAWEATGAWN) (FIG. 2).

A targeting vector was constructed (FIG. 2) by replacing the above mutated TM DNA into Nar1-Spe1 digested Kpn12/BS, generating Kpn12LeD/BS. The 3.5 kb Spe1-Spe1 fragment of 3' homology was excised from Kpn12LeD/BS, and the remaining vector was religated. A 1.5 kb Kpn1/BgII fragment was removed from the most 5' end of the gene, and following mung bean nuclease digestion, the ends of the vector were also relegated, resulting in approximately 3.4 kb of 5' homology. Following digestion of the latter construct with Xho1 and BgIII, a loxP-flanked neomycin phosphotransferase (nea) gene was subsequently inserted within the 3'-UTR. The resultant vector was cut with Pac1, and the previously purified 3.5 kb Spe1-Spe1 fragment representing 3'-homology, was inserted in the correct orientation. Finally, for negative selection, the gene encoding cytosine deaminase (cda) was inserted at the 3' end of the targeting vector between the Sal1 and Not1 sites.

3. Targeting of Mutated TM Gene Into Embryonic Stem (ES) Cells

Targeting vector DNA (20 μg) was linearized with Not1 and introduced into R1 ES cells by electroporation, following which the cells were plated onto confluent layers of neomycin-resistant embryonic fibroblasts in the presence of G418 and 5-fluorocytosine (5-FC). DNA from surviving colonies was screened for homologous recombination by Southern blotting using a 3' external probe E (as shown on FIG. 2). Random integrations were excluded by Southern blotting with a neomycin DNA probe and internal probes. Using DNA from the homologously recombined ES cell clones, the expected deletion was confirmed by PCR with primer pair TM.s99 (5'-GTCTAGGTTGTGATAGAGGCT) and TM.as1005 (5'-GGCAGAGGCATCTGGGTTCATT), followed by DNA sequencing of the 257 bp PCR product.

4. Introduction of Mutated TM Into Mice

Targeted ES cells were aggregated[25] with morula-stage embryos derived from C57Bl6/J mice, and introduced into pseudopregnant female National Institutes of Health (NIH) Swiss white mice. Two chimeric male offspring resulted in the establishment of germline transmission of the mutant TM allele ($TM^{LeDneo/wt}$). Large numbers of F1 and F2 offspring were intercrossed, avoiding brother-sister matings. Genotyping was performed on tail DNA both by Southern blotting and by PCR. The chimeric males were also backcrossed with C57Bl/6 and 129sv/ev mouse pedigrees for comparative purposes.

5. In Vivo Excision of loxP-flanked Neomycin Gene

Mice with a single allele replaced with the mutant $TM^{LeDneo}$ ($TM^{LeDneo/wt}$ mice) were bred with mice homozygous for ubiquitous expression of cre-recombinase under the control of the phosphoglucokinaese promoter (PGK-Cre mice)[26]. In vivo excision of the loxP-flanked neo from the $TM^{LeDneo/wt}$ mice was confirmed by PCR on genomic DNA of offspring from several tissues. The oligonucleotide primer pair TM.s2520 (sense 5' GGCTTTGGGTATTTAGTCAGA) and TM.as2700 (antisense 5' CATAAAACCCAGGCT-CACCC) yielded an amplicon of 256 bp when excision was accomplished, while the product was 174 bp in length from the wild-type allele. The resultant $TM^{LeD/wt}$ mice were intercrossed to generate mice with the TM mutation in both alleles. Wild-type siblings from these matings were used as controls ($TM^{wt/wt}$ mice) so that genetic backgrounds were identical.

6. Expression of Recombinant TM in Mammalian Cells and Quantitation of TM Levels The cDNA encoding wild-type and mutated TM were subcloned into the expression vector pcDNA3.1 (Invitrogen, CA) for transfectidn into COS cells. Serial dilution of the cells under continuous selection with G418 resulted in isolated clones of TM-expressing cells. A vector-alone control COS cell line was also generated. Expression of cell surface TM was confirmed by indirect immunofluorescence[27] using specific rabbit anti-rat TM antisera [28]. The cofactor activity of cell-surface expressed recombinant TM was evaluated by activation of purified bovine protein C with exogenously added bovine thrombin[29]. Relative amounts of TM in lung tissue and plasma were quantitated using a sandwich radio-immunoassay[30] and the polyclonal anti-rat TM antibodies.

7. RNA Isolation and RT-PCR

Total RNA was isolated from tissue by the method of Chomczynski and Sacchi[31]. For RT-PCR, cDNA was synthesized from total RNA by reverse transcription using murine leukemia virus (M-MLV) reverse transcriptase and a cDNA synthesis kit (NV Life Technologies, Belgium). First-strand synthesis was primed using random hexanucleotides. To confirm the deletion of the lectin domain of TM in the gene-targeted mice by RT-PCR, oligonucleotide primers that flank the deleted region, TM.s99 and TM.as1005, were used, and the amplicon was sequenced.

8. Isolation and Growth of Endothelial Cells

Endothelial tumors were induced to grow in 7 day old mice following intraperitoneal (i.p.) injection of retrovirus carrying the middle T antigen of murine Polyomavirus (PymT). After 10-14 days, the tumors were excised, and endothelial cells were isolated[32,33]. Primary cultures of lymphatic endothelial cells were isolated from intraperitoneal lymphangiomas, growth of which was induced by injection of incomplete Freund's adjuvant exactly as described[34]. Cells were cultured on collagen or gelatin coated plates in M199 media supplemented with 20% fetal bovine serum, porcine heparin 0.1 mg/ml, endothelial cell mitogen 5 µg/ml (Biomedical Technologies Inc., Stoughton, Mass.), 100 µg/ml penicillin and streptomycin 100 µg/ml. Cell cultures were incubated at 37° C. in a humidified atmosphere of 5% $CO_2$ and 95% air, and experiments were performed at passage 3-8. Over 95% of the cells immunostained positively for TM and vWF, confirming the endothelial origin and purity.

9. Isolation of Neutrophils and Lymphocytes from Murine Bone Marrows

Neutrophils and lymphocytes were isolated from bone marrow according to the method of Lowell and Berton [35]. Each population was assessed to be over 95% pure by microscopic analysis after Wright staining.

10. Flow Chamber Experiments

Experiments to evaluate adhesion and rolling of bone marrow-derived leukocytes on monolayers of endothelial cells in a flow chamber were performed as previously described [36]. Briefly, endothelial cells grown on collagen coated glass coverslips were mounted in a parallel flow chamber and superfused with leukocyte suspensions ($2\times10^5$ cells/mL). Interactions of BCECF-AM (Molecular Probes) labeled leukocytes with endothelial cells were observed with an inverted epifluorescence microscope and images were analyzed with NIH Image1.6. Rolling neutrophils or lymphocytes were counted on 5 overlays of video frames spanning in total 50 sec of a 5 min experiment. Firm adhesion was determined on 15 high power fields (0.9 mm$^2$) after rinsing for 5 min.

11. Static Adhesion Assay

Endothelial cells were plated in 24-well dishes and grown to confluence. Following 2 washes of the cell monolayers with HBSS, freshly prepared BCECF-AM-labeled, neutrophils derived from human peripheral blood, or murine bone marrow-derived PMNs or lymphocytes 50,000 per well, were added in a final volume of 1 ml for 30 minutes at room temperature. The media was decanted and the cell monolayers were gently washed three times with HBSS after which the adherent fluorescently labeled leukocytes were counted with an inverted epiflourescence microscope as described above.

12. In Vivo Activation of Protein C

Human protein C, 100 µg, was injected intravenously into mice and 15 minutes later, citrated plasma was obtained. To detect plasma levels of activated human protein C, a specific and sensitive capture immunoassay with Mab 7D7B10 was used[16,37]. Plasma levels of human protein C in murine plasma were measured using the Coamatic Protein C Assay Kit (Chromogenix, Molndal, Sweden) according to the manufacturer's instructions, except that the standard curve was generated by diluting known quantities of purified human protein C in pooled murine plasma. Results of both assays reflect measures performed in duplicate on a minimum of 5 mice with each genotype under different conditions.

13. Quantitation of Plasma Levels of Cytokines and Fibrinopeptide A

Double antibody sandwich ELISA kits, purchased from R & D Systems Europe (Abingdon, UK), were used to quantitate murine plasma levels of TNFα, IL-1β, IL-6 and IL-10. Controls were provided. A sensitive and specific radioimmunoassay to quantitate plasma levels of murine FPA was performed as previously reported[24].

14. Thrombogenic Stresses

Mice were exposed to 5.5% oxygen for 16-18 hours in a normobaric chamber[38], after which they were immediately anesthetized. The sternum was split for cardiac puncture to withdraw blood into appropriate anticoagulants for subsequent assays. The vasculature was perfused via the heart with PBS. Tissues were quickly dissected and either fixed for histological analysis or placed into liquid nitrogen for protein or RNA studies. Tissue levels of fibrin were determined as reported[16]. Transverse sections of the lungs were cut and stained for detection of neutrophils and monocytes with myeloperoxidase, or for TM or fibrinogen by immunoperoxidase staining using specific antibodies.

15. Endotoxin Studies

Lipopolysaccharide (LPS) from *Escherichia coli* serotype 0111:B4 (Sigma) was injected intraperitoneally into 10-12 week old mice. For lethality studies, animals were closely monitored each day until either recovery or cessation of breathing. To study the effects of endotoxin-induced lung inflammation, endotoxin solution 1 mg/ml was nebulized into the mice housing for 10 minutes, 3 hours after which the mice were sacrificed by urethane overdose. Blood samples were drawn and the lungs were lavaged 5 times through a tracheal catheter with 1 ml of PBS with 5% BSA at 37° C. Bronchoalveolar lavage (BAL) was centrifuged at 4000 g for 5 minutes, washed and resuspended in 200 μl of PBS, fractions of which were used for differential cell count and myeloperoxidase activity assay by slight modification of the technique of Bradley et al.[39]. Lungs were dissected and fixed overnight for paraffin embedding and histological analyses.

16. Myocardial Ischemia/Reperfusion (MI/R) Studies

Myocardial ischemia was induced surgically as reported[40]. Briefly, mice were intubated and ventilated using a Minivent (Hugo Sachs Electronic, March-Hugstetten, Germany). Body temperature was maintained at 36° C. throughout the experiment. The left anterior descending coronary artery (LAD) was exposed through a limited left thoracotomy, and ligated over PE-10 tubing. Ischemia of the left ventricle (LV), evident by blanching and dyskinesis, was maintained for 30 minutes, after which the PE-10 tubing was removed, leaving the suture in place, while allowing reperfusion. Three hours later, the abdominal aorta was catherterized and heparinized saline was infused until no blood was collected from a caval venotomy at the level of the renal vessels. The LAD was reoccluded and 3 mL of Evans blue was injected into the aortic catheter to delineate the area at risk. The heart was carefully excised, cut into 1 mm thick slices and immersed in 2% tetrazoliumchloride for 20 minutes[41]. Area at risk, infarct area and LV area were determined by planimetry of digitized images of the slices using NIH lmgage 1.62 software.

17. Wound-healing in Mice

Under anesthesia, circular 2 cm diameter incisions were made on the back, through the skin to the depth of the dermis. Mice were then housed in separate cages to prevent scratching, and over the ensuing 9 days, the wounds were regularly inspected, and the area of each wound was determined.

18. Generation of Recombinant Lectin Domain of TM

Two "mini-proteins" derived from the N-terminal domain of murine TM were generated by the *Pichia pastoris* expression system (Invitrogen, CA). For the first ($TM_{lec223}$), the PCR-generated cDNA fragment encoding amino acids 1-223 of the mature protein (lacking the putative signal peptide) and thus representing the lectin-like domain plus the adjacent hydrophobic region, was subcloned in-frame into the *Pichia pastoris* expression vector pICZαA. For the second ($TM_{lec155}$), PCR-generated cDNA encoding the first 155 amino acids of murine TM, i.e. restricted to the lectin-like region, was subcloned into pICZαA. In both cases, a polyhistidine-tag was present at the carboxy-terminus of the recombinant protein. Expression was confirmed by Western immunoblotting with the polyclonal anti-rat TM antisera. Purification of the expressed proteins to high degree, as evaluated by silver staining was accomplished by the following: A final concentration of 1 M ammonium sulfate was added to approximately 1 litre of *Pichia pastoris* culture media containing the expressed protein, which was then passed over a 1.6 cm×10 cm phenyl-sepharose column. The gel was washed with a buffer containing 10 mM Na-phosphate pH 7.0 and 1 M ammonium sulfate. Partially purified protein was subsequently eluted step-wise with 10 mM Na-phosphate buffer pH 7.0, and the peak was desalted on a 2.5 cm×30 cm G25 column, washed with a buffer containing 10 mM Na-phosphate pH 7.0, 0.01% Tween 80. The desalted protein fractions were pooled and run over a 1.0 cm×2.0 cm fast-flow Q-sepharose column, extensively washed with 10 mM Na-phosphate pH 7.0, 0.01% Tween 80, and the protein was eluted using a salt gradient of 0 to 1.0 M NaCl over 20 mls buffer containing 10 mM Na-phosphate pH 7.0. The fractions containing the desired protein, identified by SDS-PAGE and Western immunoblotting, were pooled, lyophilized, suspended in a total volume of 3 ml $H_2O$, and size fractionated on a superdex 75 1.6×94 cm column, using a running buffer of PBS+0.01% Tween 80. Those fractions that yielded the appropriate apparent molecular weight of the desired protein by SDS-PAGE analysis and Western immunoblot, were pooled and frozen for subsequent studies.

In a second approach, the cDNA encoding the first 155 amino acids of TM was subcloned into the vector pGEX-4T-3 for generation of a GST-fusion protein in *Eschericia coli*. Following expression, the media containing the fusion protein ($TM_{lec155}$-GST) was incubated with glutathione-sepharose, washed, and the $TM_{lec155}$-GST was eluted from the sepharose beads with excess free glutathione. Purity was assessed by silver staining and Western immunoblotting.

19. Animal Care

All animal experiments were approved by the Institutional Animal Care and Use Committee of the University of Leuven.

20. Statistical Analyses

Statistical analyses of data using standard methods, were conducted with the StatView computer program (Abacus Concepts Inc., CA) or InStat 2.03 (GraphPad Software, San Diego, Calif.). The means are provided with associated standard errors (SD). p-values were determined using the unpaired t-test and groupwise comparisons were performed by Wilcox-ranked sum testing.

Tables

TABLE 1

| Mice | Fibrin (µg/gm) (n = 10) | FPA (nmol/L) (n = 10) |
|---|---|---|
| $TM^{wt/wt}$ | 25 ± 17 | 3.2 ± 2.1 |
| $TM^{wt/wt}$ + hypoxia | 46 ± 28 | 3.3 ± 2.3 |
| $TM^{LeD/LeD}$ | 36 ± 24 | 4.6 ± 2.5 |
| $TM^{LeD/LeD}$ + hypoxia | 28 ± 21 | 5.2 ± 4.2 |

TABLE 2

| Mice | Fibrin (µg/gm) (n = 8) |
|---|---|
| $TM^{wt/wt}$ | 32 ± 28 |
| $TM^{wt/wt}$ + hypoxia | 42 ± 23 |
| $TM^{LeD/LeD}$ | 56 ± 20 |
| $TM^{LeD/LeD}$ + hypoxia | 26 ± 37 |

TABLE 3

| Mice | TNFα (ng/ml) | IL-1β (ng/ml) | IL-10 (ng/ml) | WBC (×10³/µl) |
|---|---|---|---|---|
| $TM^{wt/wt}$ + LPS | 63 ± 21 | 87 ± 32 | 110 ± 68 | 0.6 ± 0.4 |
| $TM^{LeD/LeD}$ + LPS | 255 ± 91 | 213 ± 68 | 138 ± 42 | 1.2 ± 0.5 |
| $TM^{LeDneo/LeDneo}$ + LPS | 318 ± 85 | 404 ± 116 | 116 ± 40 | 0.9 ± 0.4 |

TABLE 4

| Mice | MPO Activity (OD units) |
|---|---|
| $TM^{wt/wt}$ (n = 3) | 87 ± 17 |
| $TM^{wt/wt}$ LPS (n = 8) | 120 ± 50 |
| $TM^{Led/Led}$ (n = 4) | 92 ± 23 |
| $TM^{Led/Led}$ LPS (n = 8) | 420 ± 31 | p < 0.05; p < 0.005

TABLE 5

| Mice | hPC (µg/ml) | hAPC (ng/ml) | hAPC after LPS (ng/ml) |
|---|---|---|---|
| $TM^{wt/wt}$ | 8.6 ± 1.3 | 7.8 ± 2.0 | 14.0 ± 0.4 |
| $TM^{LeD/LeD}$ | 9.2 ± 1.8 | 5.4 ± 1.8 | 12.9 ± 5.1 |
| $TM^{LeDneo/LeDneo}$ | 7.9 ± 2.2 | 6.0 ± 0.4 | 16.2 ± 4.7 |

TABLE 6

| Endothelial Cells | Source of PMNs | PMN Adhesion (# per 15 HPFs) |
|---|---|---|
| fEND.5 cells – resting | $TM^{wt/wt}$ mice | 62 ± 6 |
|  | $TM^{LeD/LeD}$ mice | 63 ± 8[#] |
| fEND.5 cells + TNFα | $TM^{wt/wt}$ mice | 101 ± 6[&] |
|  | $TM^{LeD/LeD}$ mice | 121 ± 7[&#] |

[&] $p < 0.01$ vs resting fEND.5 cells
[#] $p > 0.5$ vs PMNs from $TM^{wt/wt}$ mice on corresponding fEND.5 cells

TABLE 7

| Source of Endothelial Cells (Genotype of mice) +/– TNF treated | PMN Adhesion (# per 15 HPFs) | p-values for corresponding result | | |
|---|---|---|---|---|
| | | $TM^{wt/wt}$ + TNF | $TM^{Led/Led}$ | $TM^{Led/Led}$ + TNF |
| $TM^{wt/wt}$ | 36 ± 31 | <0.05 | <0.02 | <0.001 |
| $TM^{wt/wt}$ + TNF | 246 ± 216 |  | >0.5 | <0.001 |
| $TM^{LeD/LeD}$ | 283 ± 231 |  |  | <0.001 |
| $TM^{LeD/LeD}$ + TNF | 767 ± 166 |  |  |  |

TABLE 8

| Source of Endothelial Cells (Genotype of mice) +/– TNF treated | PMN Adhesion (# per 15 HPFs) | Lymphocyte Adhesion (# per 15 HPFs) |
|---|---|---|
| $TM^{wt/wt}$ | 15 ± 4 | 3 ± 1 |
| $TM^{wt/wt}$ + TNF | 171 ± 37 | 31 ± 12 |
| $TM^{LeD/LeD}$ | 52 ± 18 | 8 ± 3 |
| $TM^{LeD/LeD}$ + TNF | 182 ± 38 | 35 ± 13 |
| $TM^{wt/wt}$ + anti-TM ab | 44 ± 8 |  |
| $TM^{wt/wt}$ + preimmune ab | 9 ± 6 |  |
| $TM^{LeD/LeD}$ + anti-TM ab | 69 ± 14 |  |

TABLE 9

| Source of Endothelial Cells | Recombinant $TM_{lec155}$ | PMN Adhesion (# per 15 HPFs) |
|---|---|---|
| $TM^{wt/wt}$ |  | 10 ± 6 |
| $TM^{LeD/LeD}$ |  | 39 ± 21 |
| $TM^{LeD/LeD}$ | 3.6 mg | 15 ± 6 |
| $TM^{LeD/LeD}$ | 7.2 mg | 12 ± 7 |
| $TM^{LeD/LeD}$ + TNF |  | 212 ± 53 |
| $TM^{LeD/LeD}$ + TNF | 3.6 mg | 132 ± 90 |
| $TM^{LeD/LeD}$ + TNF | 7.2 mg | 153 ± 106 | p < 0.001; p = .017; p < 0.00
p < 0.001; p = 0.28; p < 0.001

TABLE 10

| Treatment | IL-1β (ng/ml) | |
|---|---|---|
| PBS | 174 +/− 108 (n = 6) | p = 0.02 |
| TM$_{lec155}$ | 286 +/− 75 (1 = 5) | |

TABLE 11

PMN Adhesion to LPS-stimulated fEND.5 Cells
hTM Fragment #1: (1.226-680 bp) (Seq ID N°:1)

| | Count | Mean | Std. Dev. | Std. Err. |
|---|---|---|---|---|
| assay buffer | 54 | 52.315 | 30.372 | 4.133 |
| pr. 680 bp 5 μg | 72 | 29.403 | 32.707 | 3.855 |
| pr. 680 bp 8 μg | 72 | 24.292 | 22.404 | 2.040 |
| pr. 680 bp 15 μg | 69 | 18.333 | 18.033 | 2.171 |

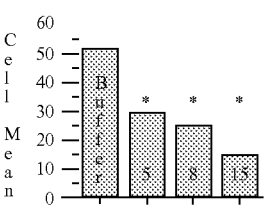

| | Mean Diff. | Crit. Diff. | P-Value | |
|---|---|---|---|---|
| assay buffer, pr. 680 bp 5 μg | 22.912 | 9.340 | <.0001 | S |
| assay buffer, pr. 680 bp 8 μg | 28.023 | 9.340 | <.0001 | S |
| assay buffer, pr. 680 bp 15 μg | 33.981 | 9.427 | <.0001 | S |
| pr. 680 bp 5 μg, pr. 680 bp 8 μg | 5.111 | 8.647 | .2455 | |
| pr. 680 bp 5 μg, pr. 680 bp 15 μg | 11.069 | 8.741 | .0133 | S |
| pr. 680 bp 8 μg, pr. 680 bp 15 μg | 5.958 | 8.741 | .1807 | |

TABLE 12

PMN Adhesion to TNF-stimulated fEND.5 Cells
hTM Fragment #1: (1.226-680 bp) (Seq ID N°:1)

| | Count | Mean | Std. Dev. | Std. Err. |
|---|---|---|---|---|
| Assay buffer | 65 | 98.723 | 100.098 | 12.416 |
| Pr. 680 bp 5 μg | 32 | 85.656 | 79.996 | 14.141 |
| Pr. 680 bp 10 μg | 33 | 24.303 | 27.845 | 4.847 |

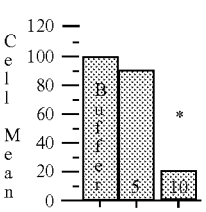

| | Mean Diff. | Crit. Diff. | P-value | |
|---|---|---|---|---|
| Assay buffer, pr. 680 bp 5 μg | 13.067 | 35.256 | .4647 | |
| Assay buffer, pr. 680 bp 10 μg | 74.420 | 34.896 | <.0001 | S |
| Pr. 680 bp 5 μg, pr. 680 bp 10 μg | 61.353 | 40.504 | .0033 | S |

TABLE 13

PMN Adhesion to LPS-Stimulated fEND.5 Cells
hTM Fragment #2: (1.159-480 bp) (SEQ ID N° 2)

| | Count | Mean | Std. Dev. | Std. Err. |
|---|---|---|---|---|
| assay buffer | 54 | 52.31 | 30.37 | 4.13 |
| pr. 480 bp 5 μg | 54 | 27.68 | 16.04 | 2.18 |
| pr. 480 bp 8 μg | 54 | 25.50 | 14.84 | 2.02 |
| pr. 480 bp 15 μg | 52 | 19.01 | 14.00 | 1.94 |

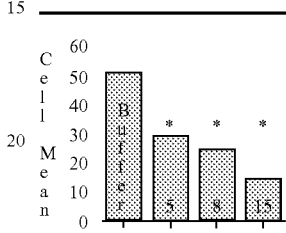

| | Mean Diff. | Crit. Diff. | P-Value | |
|---|---|---|---|---|
| assay buffer, pr. 480 bp 5 μg | 24.63 | 7.598 | <.0001 | S |
| assay buffer, pr. 480 bp 8 μg | 26.815 | 7.598 | <.0001 | S |
| assay buffer, pr. 480 bp 15 μg | 33.296 | 7.670 | <.0001 | S |
| pr. 480 bp 5 μg, pr. 480 bp 8 μg | 2.185 | 7.598 | .5713 | |
| pr. 480 bp 5 μg, pr. 480 bp 15 μg | 8.666 | 7.670 | .0270 | S |
| pr. 480 bp 8 μg, pr. 480 bp 15 μg | 6.48 | 7.670 | .0973 | |

TABLE 14

PMN Adhesion to LPS-Stimulated fEND.5 Cells
hTM Fragment #4: (33.159-400 bp) (SEQ ID N° 4)

| | Count | Mean | Std. Dev. | Std. Err. |
|---|---|---|---|---|
| assay buffer | 53 | 44.887 | 30.905 | 4.245 |
| prot. 400 bp 5 μg | 53 | 33.642 | 25.119 | 3.450 |
| prot. 400 bp 8 μg | 51 | 29.725 | 19.183 | 2.686 |

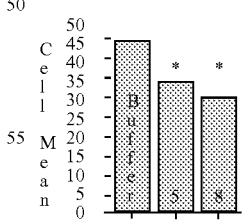

| | Mean Diff. | Crit. Diff. | P-value | |
|---|---|---|---|---|
| assay buffer, prot. 400 bp 5 μg | 11.245 | 9.822 | .0251 | S |
| assay buffer, prot. 400 bp 8 μg | 15.161 | 9.918 | .0030 | S |
| prot. 400 bp 5 μg, prot. 400 bp 8 μg | 3.916 | 9.918 | .4366 | |

TABLE 15

PMN Adhesion to TNF-Stimulated fEND.5 Cells
hTM Fragment #4: (33.159-400 bp) (SEQ ID N° 4)

|  | Count | Mean | Std. Dev. | Std. Err. |
|---|---|---|---|---|
| assay buffer | 65 | 98.723 | 100.098 | 12.416 |
| pr. 400 bp 8 µg | 36 | 53.417 | 45.182 | 7.530 |
| pr. 400 bp 20 µg | 32 | 63.500 | 54.004 | 9.547 |

|  | Mean Diff. | Crit. Diff. | P-Value |  |
|---|---|---|---|---|
| assay buffer, pr. 400 bp 8 µg | 45.306 | 32.306 | .0063 | S |
| assay buffer, pr. 400 bp 20 µg | 35.223 | 33.580 | .0399 | S |
| pr. 400 bp 8 µg, pr. 400 bp 20 µg | −10.083 | 37.780 | .05984 |  |

TABLE 16

PMN Adhesion to LPS-Stimulated fEND.5 Cells
hTM Fragment #3; Peptide #24: (3.33) (SEQ ID N° 3)

|  | Count | Mean | Std. Dev. | Std. Err. |
|---|---|---|---|---|
| assay buffer | 53 | 44.887 | 30.905 | 4.245 |
| pept. N° 24, 1 µg | 53 | 38.830 | 26.390 | 3.625 |
| pept. N° 24, 5 µg | 53 | 44.019 | 31.623 | 4.344 |
| Pept. N° 24, 8 µg | 52 | 22.000 | 19.164 | 2.658 |

|  | Mean Diff. | Crit. Diff. | P-Value |  |
|---|---|---|---|---|
| assay buffer, pept. N° 24, 1 µg | 6.057 | 10.534 | .2583 |  |
| assay buffer, pept. N° 24, 5 µg | .868 | 10.534 | .8711 |  |
| assay buffer, pept. N° 24, 8 µg | 22.887 | 10.585 | <.0001 | S |
| pept. N° 24, 1 µg, pept. N° 24, 5 µg | −5.189 | 10.534 | .3326 |  |
| pept. N° 24, 1 µg, pept. N° 24, 8 µg | 16.830 | 10.585 | .0020 | S |
| pept. N° 24, 5 µg, pept. N° 24, 8 µg | 22.019 | 1.585 | <.0001 | S |

TABLE 17

PMN Adhesion to LPS-Stimulated fEND.5 Cells
hTM Fragment #7, Peptide #23: (84.97) (SEQ ID N° 7)

|  | Count | Mean | Std. Dev. | Std. Err. |
|---|---|---|---|---|
| assay buffer | 71 | 44.394 | 25.781 | 3.060 |
| pept n° 23, 1 µg | 68 | 31.015 | 23.525 | 2.853 |
| pept n° 23, 5 µg | 71 | 21.535 | 13.302 | 1.579 |

|  | Mean Diff. | Crit. Diff. | P-Value |  |
|---|---|---|---|---|
| assay buffer | 13.380 | 7.204 | .0003 | S |
| assay buffer, pept n° 23, 5 µg | 22.859 | 7.125 | <.0001 | S |
| pept n° 23, 1 µg, pept n° 23, 5 µg | 9.479 | 7.204 | .0102 | S |

REFERENCES

1. Wen D, Dittman W A, Ye R D, Deaven L L, Majerus P W, Sadler J E. Human thrombomodulin: Complete cDNA sequence and chromosome localization of the gene. Biochem. 1987;6:2960-2967
2. Suzuki K, Kusomoto H, Deyashiki Y, Hishioka J, Maruyama I, Zushi M, Kawahara S, Honda G, Yamamoto S, Horiguchi S. Structure and expression of human thrombomodulin, a thrombin receptor on endothelium acting as a cofactor for protein C activation. EMBO J. 1987;6: 1891-1897
3. Petersen T. The amino-terminal domain of thrombomodulin and pancreatic stone protein are homologous with lectins. FEBS. 1988;231:51-53
4. Patthy L. Detecting distant homologies of mosaic proteins. Analysis of the sequences of thrombomodulin, thrombospondin, complement components C9, C8 alpha and C8 beta, vitronectin and plasma cell membrane glycoprotein PC-1. J. Mol. Biol. 1988,202:689-696
5. Conway E, Pollefeyt S, Collen D, Steiner-Mosonyi M. The amino terminal lectin-like domain of thrombomodulin is required for constitutive endocytosis. Blood. 1997; 89:652-661
6. Chu M, Bird C H, Teasdale M, Bird P I. Turnover of thrombomodulin at the cell surface occurs at a similar rate to receptors that are not actively internalized. Thromb Haemost. 1998;80:119-127
7. Lu R, Esmon N L, Esmon C T, Johnson A E. The active site of the thrombin-thrombomodulin complex. J. Biol. Chem. 1989;264:12956-12962
8. Kokame K, Zheng X, Sadler J. Activation of thrombin-activatable fibrinolysis inhibitor requires epidermal growth factor-like domain-3 of thrombomodulin and is inhibited competitively by protein C. J. Biol. Chem. 1998;273:12135-12139
9. Kurosawa S, Stearns D J, Jackson K W, Esmon C T. A 10-kDa cyanogen bromide fragment from the epidermal growth factor homology domain of rabbit thrombomodulin contains the primary thrombin binding site. J. Biol. Chem. 1988;263:5993-5996

10. Zushi M, Gomi K, Yamamoto S, Maruyama I, Hayashi T, Suzuki K. The last three consecutive epidermal growth factor-like structures of human thrombomodulin comprise the minimum functional domain for protein C-activating cofactor activity and anticoagulant activity. J. Biol. Chem. 1989;264:10351-10353

11. Suzuki K, Hayashi T, Nishioka J, Kosaka Y, Zushi M, Honda G, Yamamoto S. A domain composed of epidermal growth factor-like structures of human thrombomodulin is essential for thrombin binding and for protein C activation. J. Biol. Chem. 1989;264:4872-4876

12. Tsiang M, Lentz S R, Sadler J E. Functional domains of membrane-bound human thrombomodulin. EGF-like domains four to six and the serine/threonine-rich domain are required for cofactor activity. J Biol Chem. 1992;267: 6164-6170

13. Conway E, Nowakowski B, Steiner-Mosonyl M. Thrombomodulin lacking the cytoplasmic domain efficiently internalizes thrombin via nonclathrin-coated, pit-mediated endocytosis. J. Cell. Phys. 1994;158:285-298

14. Isermann B, Hendrickson S B, Hutley K, Wing M, Weiler H. Tissue-restricted expression of thrombomodulin in the placenta rescues thrombomodulin-deficient mice from early lethality and reveals a secondary developmental block. Development. 2001;128:827-838

15. Healy A, Rayburn H, Rosenberg R, Weiler H. Absence of the blood-clotting regulator thrombomodulin causes embryonic lethality in mice before development of a functional cardiovascular system. Proc. Natl. Acad. Sci. (USA). 1995;92:850-854

16. Weiler-Guettler H, Christie P, Beeler D, Healy A, Hancock W, Rayburn H, Edelberg J, Rosenberg R. A targeted point mutation in thrombomodulin generates viable mice with a prethrombotic state. J. Clin. Invest. 1998;101:1-9

17. Rosenberg R. Thrombomodulin gene disruption and mutation in mice. Thromb. Haemostasis. 1997;78:705-709

18. Boffa M-C, Burke B, Haudenschild C. Preservation of thrombomodulin antigen on vascular and extravascular surfaces. J. Histochem. Cytochem. 1987;35:1267-1276

19. Imada M, Imada S, Iwasaki H, Kume A, Yamaguchi H, Moore E. Fetomodulin: Marker surface protein of fetal development which is modulatable by cyclic AMP. Dev. Biol. 1987;122:483-491

20. Imada S, Yamaguchi H, Nagumo M, Katayanagi S, Iwasaki H, Imada M. Identification of fetomodulin, a surface marker protein of fetal development, as thrombomodulin by gene cloning and functional assays. Dev Biol. 1990;140:113-122

21. Zhang Y, Weiler-Guettler H, Chen J, Wilhelm O, Deng Y, Qiu F, Nakagawa K, Kievesath M, Wilhelm S, Bohrer H, Nakagawa M, Graeff H, Martin E, Stern D, Rosenberg R, Ziegler R, Nawroth P. Thrombomodulin modulates growth of tumor cells independent of its anticoagulant activity. J. Clin. Invest. 1998;101:1301-1309

22. Waugh J M, Yuksel E, Li J. Kuo M D, Kattash M, Saxena R, Geske R, Thung S N, Shenaq S M, Woo S L. Local overexpression of thrombomodulin for in vivo prevention of arterial thrombosis in a rabbit model. Circ Res. 1999; 84:84-92

23. Ford V, Kennel S. An intracisternal A-particle DNA sequence is closely linked to the thrombomodulin gene in some strains of laboratory mice. DNA Cell Biol. 1993; 12:311-318

24. Conway E M, Pollefeyt S, Cornelissen J, DeBaere I, Steiner-Mosonyi M, Weitz J I, Weiler-Guettler H, Carmeliet P, Colhen D. Structure-function analyses of thrombomodulin by gene-targeting in mice: the cytoplasmic domain is not required for normal fetal development. Blood. 1999;93:3442-3450

25. Wood S, Allen N, Rossant J, Auerbach A, Nagy A. Non-injection methods for the production of embryonic stem cell-embryo chimaeras. Nature. 1993;365:87-89

26. Lallemand Y, Luria B. Haffner-Krausz R, Lonai P. Maternally expressed PGK-Cre transgene as a tool for early and uniform activation of the Cre site-specific recombinase. Transgenic Res. 1998;7:105-112

27. Conway E, Boffa M, Nowakowski B, Steiner-Mosonyi M. An ultrastructural study of thrombomodulin endocytosis: Internalization occurs via clathrin-coated and non-coated pits. J. Cell. Phys. 1992;151:604-612

28. Jackman R W, Stapleton T D, Masse E M, Harvey V S, Meyers M S, Shockley T R, Nagy J A. Enhancement of the functional repertoire of the rat parietal peritoneal mesothelium in vivo: directed expression of the anticoagulant and antiinflammatory molecule thrombomodulin [In Process Citation]. Hum Gene Ther. 1998;9:1069-1081

29. Conway E M, Rosenberg R D. Tumor necrosis factor suppresses transcription of the thrombomodulin gene in endothelial cells. Mol. Cell Biol. 1988;8:5588-5592

30. Kennel S, Lankford T, Hughes B, Hotchkiss J. Quantitation of a murine lung endothelial cell protein, P112, with a double monoclonal antibody assay. Lab. Investigation. 1988;59:692-701

31. Chomczynski P, Sacchi N. Single-step method of RNA isolation by acid guanidinium thiocyanate-pheno-chloroform extraction. Analyt. Biochem. 1987;162:156-159

32. Muhiner U, Mohle-Steinlein U, Wizigmann-Voos S, Christofori G. Risau W, Wagner E F. Formation of transformed endothelial cells in the absence of VEGFR-2/Flk-1 by Polyoma middle T oncogene. Oncogene. 1999; 18:4200-4210

33. Wagner E F, Risau W. Oncogenes in the study of endothelial cell growth and differentiation. Semin Cancer Biol. 1994;5:137-145

34. Mancardi S, Stanta G, Dusetti N, Gestagno M, Jussila L, Zweyer M, Lunazzi G, Dumont D, Alitalo K, Burrone S. Lymphatic endothelial tumors induced by intraperioteal injection of Freund's adjuvant. Exp. Cell Res. 1999;246: 368-375

35. Lowell C A, Berton G. Resistance to endotoxic shock and reduced neutrophil migration in mice deficient for the Src-family kinases Hck and Fgr. Proc Natl Acad Sci U S A. 1998;95:7580-7584

36. Theilmeier G, Lenaerts T, Remacle C, Colhen D, Vermylen J, Hoylaerts M F. Circulating activated platelets assist THP-1 monocytoid/endothelial cell interaction under shear stress. Blood. 1999;94:2725-2734

37. Orthner C L, Kolen B, Drohan W N. A sensitive and facile assay for the measurement of activated protein C activity levels in vivo. Thromb Haemost. 1993;69:441-447

38. Lawson C, Yan S, Yan S, Liao H, Zhou Y, Sobel J, Kisiel W, Stern D, Pinsky D. Monocytes and tissue factor promote thrombosis in a murine model of oxygen deprivation. J. Clin. Invest. 1997;99:1729-1738

39. Bradley P P, Priebat D A, Christensen R D, Rothstein G. Measurement of cutaneous inflammation: estimation of neutrophil content with an enzyme marker. J Invest Dermatol. 1982;78:206-209

40. Michael L H, Entman M L, Hartley C J, Youker K A, Zhu J, Hall S R, Hawkins H K, Berens K, Ballantyne C M. Myocardial ischemia and reperfusion: a murine model. Am J Physiol. 1995;269:H2147-2154.

41. Fishbein M C, Meerbaum S, Rit J, Lando U, Kanmatsuse K, Mercier J C, Corday E, Ganz W. Early phase acute myocardial infarct size quantification: validation of the triphenyl tetrazolium chloride tissue enzyme staining technique. Am Heart J. 1981;101:593-600.
42. Raife T J, Lager D J, Madison K C, Piefte W W, Howard E J, Sturm M T, Chen Y, Lentz S R. Thrombomodulin expression by human keratinocytes. Induction of cofactor activity during epidermal differentiation. J Clin Invest. 1994;93:1846-1851
43. Peterson J J, Rayburn H B, Lager D J, Raife T J, Kealey G P, Rosenberg R D, Lentz S R. Expression of thrombomodulin and consequences of thrombomodulin deficiency during healing of cutaneous wounds. Am J Pathol. 1999; 155:1569-1575.
44. Esmon C T. Regulation of blood coagulation [In Process Citation]. Biochim Biophys Acta. 2000;1477:349-360
45. Taylor F B, Chang A, Esmon C T, D'Angelo A, Vigano-D'Angelo S, Blick K E. Protein C prevents the coagulopathic and lethal effects of *Escherichia coli* infusion in the baboon. J Clin Invest. 1987;79:918-925.
46. Taylor F, Chang A, Ruf W, Morrissey J, Hinshaw L, Catlett R, Blick K, Edgington T. Lethal *E. coli* septic shock is prevent by blocking tissue factor with monoclonal antibody. Circ. Shock. 1991;33:127-134
47. Taylor F B. Studies on the inflammatory-coagulant axis in the baboon response to *E. coli*: regulatory roles of proteins C, S, C4bBP and of inhibitors of tissue factor. Prog Clin Biol Res. 1994;388:175-194
48. Murakami K, Okajima K, Uchiba M, Johno M, Nakagaki T, Okabe H, Takatsuki K. Activated protein C prevents LPS-induced pulmonary vascular injury by inhibiting cytokine production. Am J Physiol. 1997;272:L197-202
49. Mesters R M, Helterbrand J, Utterback B G, Yan B, Chao Y B, Fernandez J A, Griffin J H, Hartman D L. Prognostic value of protein C concentrations in neutropenic patients at high risk of severe septic complications. Crit Care Med. 2000;28:2209-2216.
50. Bernard G R, Vincent J L, Laterre P F, LaRosa S P, Dhainaut J F, Lopez-Rodriguez A, Steingrub J S, Garber G E, Helterbrand J D, Ely E W, Fisher C J, Jr. Efficacy and safety of recombinant human activated protein C for severe sepsis. N Engl J Med. 2001;344:699-709.
51. White B, Livingstone W, Murphy C, Hodgson A, Rafferty M, Smith O P. An open-label study of the role of adjuvant hemostatic support with protein C replacement therapy in purpura fulminans-associated meningococcemia. Blood. 2000;96:3719-3724.
52. Grinnell B W, Hermann R B, Yan S B. Human protein C inhibits selectin-mediated cell adhesion: role of unique fucosylated oligosaccharide. Glycobiology. 1994;4:221-225.
53. Hancock W W, Grey S T, Hau L, Akalin E, Orthner C, Sayegh M H, Salem H H. Binding of activated protein C to a specific receptor on human mononuclear phagocytes inhibits intracellular calcium signaling and monocyte-dependent proliferative responses. Transplantation. 1995; 60:1525-1532.
54. Uchiba M, Okajima K, Murakami K, Johno M, Okabe H, Takatsuki K. Recombinant thrombomodulin prevents endotoxin-induced lung injury in rats by inhibiting leukocyte activation. Am J Physiol. 1996;271:L470475
55. Schmidt-Supprian M, Murphy C, While B, Lawler M, Kapurniotu A, Voelter W, Smith O, Bernhagen J. Activated protein C inhibits tumor necrosis factor and macrophage migration inhibitory factor production in monocytes. Eur Cytokine Netw. 2000;11 :407-413.
56. Taylor F B, Jr., Stearns-Kurosawa D J, Kurosawa S, Ferrell G, Chang A C, Laszik Z, Kosanke S, Peer G, Esmon C T. The endothelial cell protein C receptor aids in host defense against *Escherichia coli* sepsis. Blood. 2000;95:1680-1686
57. Gu J M, Katsuura Y, Ferrell G L, Grammas P, Esmon C T. Endotoxin and thrombin elevate rodent endothelial cell protein C receptor mRNA levels and increase receptor shedding in vivo. Blood. 2000;95:1687-1693
58. Esmon C T. The endothelial cell protein C receptor. Thromb Haemost. 2000;83:639-643.
59. Kurosawa S, Esmon C T, Stearns-Kurosawa D J. The soluble endothelial protein C receptor binds to activated neutrophils: involvement of proteinase-3 and CD1b/CD18. J Immunol. 2000;165:4697-4703.
60. Nawroth P, Stern D. Modulation of endothelial cell hemostatic properties by tumor necrosis factor. J. Exp. Med. 1986;163:740-745
61. Abe H, Okajima K, Okabe H, Takatsuki K, Binder B R. Granulocyte proteases and hydrogen peroxide synergistically inactivate thrombomodulin of endothelial cells in vitro. J Lab Clin Med. 1994;123:874-881.
62. Glaser C, Morser J, Clarke J, Blasko E, McLean K, Kuhn I, Chang R-J, Lin J-H, Vilander L, Andrews W, Light D. Oxidation of a specific methionine in thrombomodulin by activated neutrophil products blocks cofactor activity. J. Clin. Invest. 1992;90:2565-2573
63. Hasegawa N, Kandra T G, Husari A W, Veiss S, Hart W T, Hedgpeth J, Wydro R, Raffin T A. The effects of recombinant human thrombomodulin on endotoxin-induced multiple-system organ failure in rats. Am J Respir Crit Care Med. 1996;153:1831-1837.
64. Uchiba M, Okajima K, Murakami K, Nawa K, Okabe H, Takatsuki K. Recombinant human soluble thrombomodulin reduces endotoxin-induced pulmonary vascular injury via protein C activation in rats. Thromb Haemost. 1995; 74:1265-1270
65. Taoka Y, Okajima K, Uchiba M, Johno M. Neuroprotection by recombinant thrombomodulin [In Process Citation]. Thromb Haemost. 2000;83:462-468
66. Conway E, Nowakowski B, Steiner-Mosonyi M. Human neutrophils synthesize thrombomodulin that does not promote thrombin-dependent protein C activation. Blood. 1992;80:1254-1263
67. McCachren S S, Diggs J, Weinberg J B, Dittman W A. Thrombomodulin expression by human blood monocytes and by human synovial tissue lining macrophages. Blood. 1991 ;78:3128-3132
68. Grey S T, Csizmadia V, Hancock W W. Differential effect of tumor necrosis factor-alpha on thrombomodulin gene expression by human monocytoid (THP-1) cell versus endothelial cells [in Process Citation]. Int J Hematol. 1998;67:53-62
69. Porter J C, Hogg N. Integrins take partners: cross-talk between integrins and other membrane receptors. Trends Cell Biol. 1998;8:390-396
70. Moore, K. L., Esmon C T, Esmon N L. Tumor necrosis factor leads to the internalization and degradation of thrombomodulin from the surface of bovine aortic endothelial cells in culture. Blood. 1989;73:159-165
71. Redl H, Schlag G, Schiesser A, Davies J. Thrombomodulin release in baboon sepsis: its dependence on the dose of *Escherichia coli* and the presence of tumor necrosis factor. J Infect Dis. 1995;171:1522-1527
72. Lentsch A B, Ward P A. Regulation of inflammatory vascular damage. J Pathol. 2000; 190:343-348

73. Jones S P, Trocha S D, Strange M B, Granger D N, Kevil C G, Bullard DC, Lefer D J. Leukocyte and endothelial cell adhesion molecules in a chronic murine model of myocardial reperfusion injury. Am J Physiol Heart Circ Physiol. 2000;279:H2196-2201.
74. Jones S P, Girod W G, Palazzo A J, Granger D N, Grisham M B, Jourd'Heuil D, Huang P L, Lefer D J. Myocardial ischemia-reperfusion injury is exacerbated in absence of endothelial cell nitric oxide synthase. Am J Physiol. 1999;276:H1567-1573.
75. Erlich J H, Boyle E M, Labriola J, Kovacich J C, Santucci R A, Fearns C, Morgan E N, Yun W, Luther T, Kojikawa O, Martin T R, Pohiman T H, Verrier E D, Mackman N. Inhibition of the tissue factor-thrombin pathway limits infarct size after myocardial ischemia-reperfusion injury by reducing inflammation. Am J Pathol. 2000;157:1849-1862.
76. Hahn R A, MacDonald B R, Chastain M, Grinnell B W, Simpson P J. Evaluation of activated protein C on canine infarct size in a nonthrombotic model of myocardial reperfusion injury. J Pharmacol Exp Ther. 1996;276:1104-1110
77. Wu K K, Aleksic N, Ahn C, Boerwinkle E, Folsom A R, Juneja H. Thrombomodulin Ala455Val polymorphism and risk of coronary heart disease. Circulation. 2001;103:1386-1389.
78. Salomaa V, Matei C, Aleksic N, Sansores-Garcia L, Folsom A R, Juneja H, Chambless L E, Wu K K. Soluble thrombomodulin as a predictor of incident coronary heart disease and symptomless carotid artery atherosclerosis in the Atherosclerosis Risk in Communities (A RIC) Study: a case-cohort study. Lancet. 1999;353:1729-1734.
79. Kaneko H, Joubara N, Yoshino M, Yarnazaki K, Mitumaru A, Miki Y, Satake H, Shiba T. Protective Effect of Human Urinary Thrombomodulin on Ischemia-Reperfusion Injury in the Canine Liver. Eur Surg Res. 2000;32: 87-93
80. Drickamer K. Two distinct classes of carbohydrate-recognition domains in animal lectins. J. Biol. Chem. 1988;263:9557-9560
81. Galustian C, Lubineau A, le Narvor C, Kiso M, Brown G, Feizi T. L-selectin interactions with novel mono- and multisulfated Lewisx sequences in comparison with the potent ligand 3'-sulfated Lewisa. J Biol Chem. 1999;274: 18213-18217
82. Dean Y D, McGreal E P, Akatsu H, Gasque P. Molecular and cellular properties of the rat M4 antigen, a C-type lectin-like receptor with structural homology to thrombomodulin. J Biol Chem. 2000
83. Vasta G R, Quesenberry M, Ahmed H, O'Leary N. C-type lectins and galectins mediate innate and adaptive immune functions: their roles in the complement activation pathway. Dev Comp Immunol. 1999;23:401-420
84. Weisel J W, Nagaswami C, Young T A, Light D R. The shape of thrombomodulin and interactions with thrombin as determined by electron microscopy. J Biol Chem. 1996;271:31485-31490
85. Sano H, Hsu D K, Yu L, Apgar J R, Kuwabara I, Yamanaka T, Hirashima M, Liu F T. Human galectin-3 is a novel chemoattractant for monocytes and macrophages. J Immunol. 2000;165:2156-2164.
86. Kuwabara I, Liu F T. Galectin-3 promotes adhesion of human neutrophils to laminin. J Immunol. 1996;156: 3939-3944.

What is claimed is:

1. A method of treating inflammation comprising the step of administering an effective amount of a polypeptide consisting of the amino acid sequence of SEQ ID NO: 1 to a patient in need thereof.

2. The method according to claim 1 wherein said inflammation is a result of ischemia-reperfusion injury.

3. The method according to claim 1, wherein leukocyte adhesion and/or invasion is prevented.

4. The method according to claim 3 wherein said leukocyte is a neutrophil.

5. A method of treating inflammation comprising the step of administering an effective amount of a polypeptide consisting of an amino acid sequence selected from the group consisting of SEQ ID NO:2, SEQ ID NO:3, SEQ ID NO:4, SEQ ID NO:5, SEQ ID NO:6, SEQ ID NO:7, and SEQ ID NO:8 to a patient in need thereof.

6. The method according to claim 5 wherein said inflammation is a result of ischemia-reperfusion injury.

7. The method according to claim 5, wherein leukocyte adhesion and/or invasion is prevented.

8. The method according to claim 7 wherein said leukocyte is a neutrophil.

9. The method according to claim 1, wherein the polypeptide is a recombinant peptide.

* * * * *

UNITED STATES PATENT AND TRADEMARK OFFICE
CERTIFICATE OF CORRECTION

PATENT NO. : 7,341,992 B2
APPLICATION NO. : 10/478360
DATED : March 11, 2008
INVENTOR(S) : Conway et al.

It is certified that error appears in the above-identified patent and that said Letters Patent is hereby corrected as shown below:

Column 1, Line 38, "with selecting," should be changed to --with selectins,--

Column 3, Line 22, "between TMLeD/LeD" should be changed --TM$^{LeD/LeD}$--

Column 3, Line 23, "and TMwt/wt mice" should be changed to --and TM$^{wt/wt}$ mice--

Column 3, Line 26, "Between TMLeD/LeD" should be changed to --TM$^{LeD/LeD}$--

Column 3, Line 26, "TMwt/wt mice were" should be changed to --TM$^{wt/wt}$ mice were--

Column 3, Line 31, "higher in TMLeD/LeD" should be changed to --higher in TM$^{LeD/LeD}$--

Column 3, Line 31-32, "TMLeDneo/LeDneo mice." should be changed to --TM$^{LeDneo/LeDneo}$ mice.--

Column 5, Line 39, "X-ray christallography" should be changed to --X-ray crystallography--

Column 6, Line 64, "similar structure,.and" should be changed to --similar structure, and--

Column 7, Line 7, "peptide (Dean" should be changed to --peptide Dean--

Column 7, Line 45, "(eg. heart," should be changed to --(e.g., heart,--

Column 7, Line 53, "accumulated significantly." should be changed to --accumulated significantly--

Column 8, Line 12, "was signficantly higher" should be changed to --was significantly higher--

Column 8, Line 30, "with extravasafton of" should be changed to --with extravasation of--

Column 10, Line 20-21, "or wefting agent" should be changed to --or wetting agent--

Column 10, Line 24, "such as, isoprenaline," should be changed to --such as isoprenaline,--

Column 12, Line 37, "PGK promoters" should be changed to --PGK promoter$^{26}$--

UNITED STATES PATENT AND TRADEMARK OFFICE
CERTIFICATE OF CORRECTION

PATENT NO. : 7,341,992 B2
APPLICATION NO. : 10/478360
DATED : March 11, 2008
INVENTOR(S) : Conway et al.

It is certified that error appears in the above-identified patent and that said Letters Patent is hereby corrected as shown below:

Column 12, Line 37, "in FIG. 2).," should be changed to --in FIG. 2).--

Column 13, Line 16, "been signficantly altered" should be changed to --been significantly altered--

Column 13, Line 22, "and TM mice" should be changed to --and $TM^{wt/wt}$ mice--

Column 13, Line 61, "not signficantly altered." should be changed to --not significantly altered.--

Column 14, Line 1, "stimulus. TM" should be changed to --stimulus. $TM^{wt/wt}$--

Column 14, Line 6, "measurements, were not" should be changed to --measurements were not--

Column 17, Line 62, "TM rnay also have" should be changed to --TM may also have--

Column 17, Line 65, "schemia/reperfusion" should be changed to --ischemia/reperfusion--

Column 18, Line 22, "outside the MR," should be changed to --outside the AAR,--

Column 18, Line 23, "in the MR was" should be changed to --in the AAR was--

Column 18, Line 50, "murine TMlec223) is" should be changed to --murine $TM_{lec223}$) is--

Column 19, Line 24, "TM fectin-like domain" should be changed to --TM lectin-like domain--

Column 19, Line 28, "with antgen-induced" should be changed to --with antigen-induced--

Column 19, Line 46, "(designated as Tmlec)," should be changed to --(designated as $TM_{lec}$),--

UNITED STATES PATENT AND TRADEMARK OFFICE
CERTIFICATE OF CORRECTION

PATENT NO.      : 7,341,992 B2
APPLICATION NO. : 10/478360
DATED           : March 11, 2008
INVENTOR(S)     : Conway et al.

It is certified that error appears in the above-identified patent and that said Letters Patent is hereby corrected as shown below:

Column 19, Line 48, "is be initiated" should be changed to --is initiated--

Column 19, Line 49, "dose of TMlec" should be changed to --dose of $TM_{lec}$--

Column 19, Line 50, "is be administered" should be changed to --is administered--

Column 19, Line 55, "without TMlec" should be changed to --without $TM_{lec}$--

Colunm 19, Line 58, "doses of TMlec" should be changed to --doses of $TM_{lec}$--

Column 20, Line 21, "TAGTTMTTMGATCTTCCTCGAGGCGCGCCGTTCA-" should be changed to --TAGTTAATTAAGATCTTCCTCGAGGCGCGCCGTTCA- --

Column 20, Line 24, "primers TM.s-240" should be changed to --primers TMs-240--

Column 20, Line 42, "PNDQTAPLCGPLCVTVSTATEMPGEPAWEEKPCETE-" should be changed to --PNDQTAPLCGPLCVTVSTATEAAPGEPAWEEKPCETE- --

Column 20, Line 53, "were also relegated," should be changed to --were also religated--

Colunm 20, Line 56, "(nea) gene was" should be changed to --(neo) gene was--

Column 21, Line 29, "the phosphoglucokinaese" should be changed to --the phoshoglucokinase--

Column 21, Line 47, "for transfectidn into" should be changed to --for transfection into--

Column 22, Line 9, "were isolated[32,33]." should be changed to --were isolated[32,33].--

Column 22, Line 56, "inverted epiflourescence" should be changed to --inverted epifluorescence--

Column 23, Lines 6-7, "and Fibninopentide A" should be changed to --and Fibrinopeptide

A--

UNITED STATES PATENT AND TRADEMARK OFFICE
CERTIFICATE OF CORRECTION

PATENT NO. : 7,341,992 B2
APPLICATION NO. : 10/478360
DATED : March 11, 2008
INVENTOR(S) : Conway et al.

It is certified that error appears in the above-identified patent and that said Letters Patent is hereby corrected as shown below:

Column 23, Line 67, "NIH Imgage 1.62 software." should be changed to --NIH Image 1.62 software.--

Column 24, Line 40, "over 20 mis buffer" should be changed to --over 20 mls buffer--

Column 24, Line 52, "in *Eschericia*" should be changed to --in *Escherichia*--

Column 25, Line 1, "p-values were" should be changed to --P-values were--

Column 31, Line 17, "Steiner-Mosonyl M." should be changed to --Steiner-Mosonyi M.--

Column 31, Line 51, "Kievesath M," should be changed to --Klevesath M,--

Column 31, Line 56, "Li J." should be changed to --Li J,--

Column 31, Line 67, "Colhen D." should be changed to --Collen D.--

Column 32, Line 7, "Luria B." should be changed to --Luria B,--

Column 32, Lines 29-30, "thiocyanate-pheno-chloroform" should be changed to --thiocyanate-phenol-chloroform--

Column 32, Line 31, "Muhiner U," should be changed to --Muhlner U,--

Column 32, Line 32, "Christofori G." should be changed to --Christofori G,--

Column 32, Line 41, "induced by intraperioteal" should be changed to --induced by intraperitoneal--

Column 32, Line 48, "Colhen D," should be changed to --Collen D,--

Column 33, Line 6, "Piefte W W," should be changed to --Piette W W,--

Column 33, Line 62, "1996;271:L470475" should be changed to --1996;271:L470-475--

Column 34, Lines 14-15, "CD1b/CD18." should be changed to --CD11b/CD18.--

Column 35, Line 13, "Pohiman T H," should be changed to --Pohlman T H,--

UNITED STATES PATENT AND TRADEMARK OFFICE
CERTIFICATE OF CORRECTION

PATENT NO. : 7,341,992 B2
APPLICATION NO. : 10/478360
DATED : March 11, 2008
INVENTOR(S) : Conway et al.

It is certified that error appears in the above-identified patent and that said Letters Patent is hereby corrected as shown below:

Column 36, Line 1, "Yarnazaki K," should be changed to --Yamazaki K,--

Column 36, Line 15, "rat M4 antigen," should be changed to --rat AA4 antigen,--

Signed and Sealed this

Second Day of September, 2008

JON W. DUDAS
*Director of the United States Patent and Trademark Office*

SEQUENCE LISTING

```
<160> NUMBER OF SEQ ID NOS: 17

<210> SEQ ID NO 1
<211> LENGTH: 224
<212> TYPE: PRT
<213> ORGANISM: Homo sapiens
<220> FEATURE:
<221> NAME/KEY: PEPTIDE
<222> LOCATION: (1)...(224)
<223> OTHER INFORMATION: Human thrombomodulin fragment 1

<400> SEQUENCE: 1

Ala Glu Pro Gln Pro Gly Gly Ser Gln Cys Val Glu His Asp Cys Phe
 1               5                  10                  15

Ala Leu Tyr Pro Gly Pro Ala Thr Phe Leu Asn Ala Ser Gln Ile Cys
            20                  25                  30

Asp Gly Leu Arg Gly His Leu Met Thr Val Arg Ser Ser Val Ala Ala
        35                  40                  45

Asp Val Ile Ser Leu Leu Leu Asn Gly Asp Gly Gly Val Gly Arg Arg
    50                  55                  60

Arg Leu Trp Ile Gly Leu Gln Leu Pro Pro Gly Cys Gly Asp Pro Lys
65                  70                  75                  80

Arg Leu Gly Pro Leu Arg Gly Phe Gln Trp Val Thr Gly Asp Asn Asn
                85                  90                  95

Thr Ser Tyr Ser Arg Trp Ala Arg Leu Asp Leu Asn Gly Ala Pro Leu
            100                 105                 110

Cys Gly Pro Leu Cys Val Ala Val Ser Ala Ala Glu Ala Thr Val Pro
```

```
                        115                 120                 125
Ser Glu Pro Ile Trp Glu Glu Gln Gln Cys Glu Val Lys Ala Asp Gly
        130                 135                 140

Phe Leu Cys Glu Phe His Phe Pro Ala Thr Cys Arg Pro Leu Ala Val
145                 150                 155                 160

Glu Pro Gly Ala Ala Ala Ala Val Ser Ile Thr Tyr Gly Thr Pro
                165                 170                 175

Phe Ala Ala Arg Gly Ala Asp Phe Gln Ala Leu Pro Val Gly Ser Ser
                180                 185                 190

Ala Ala Val Ala Pro Leu Gly Leu Gln Leu Met Cys Thr Ala Pro Pro
                195                 200                 205

Gly Ala Val Gln Gly His Trp Ala Arg Glu Ala Pro Gly Ala Trp Asp
                210                 215                 220

<210> SEQ ID NO 2
<211> LENGTH: 157
<212> TYPE: PRT
<213> ORGANISM: Homo sapiens
<220> FEATURE:
<221> NAME/KEY: PEPTIDE
<222> LOCATION: (1)...(157)
<223> OTHER INFORMATION: Human thrombomodulin fragment 2

<400> SEQUENCE: 2

Ala Glu Pro Gln Pro Gly Gly Ser Gln Cys Val Glu His Asp Cys Phe
1               5                   10                  15

Ala Leu Tyr Pro Gly Pro Ala Thr Phe Leu Asn Ala Ser Gln Ile Cys
                20                  25                  30

Asp Gly Leu Arg Gly His Leu Met Thr Val Arg Ser Ser Val Ala Ala
            35                  40                  45

Asp Val Ile Ser Leu Leu Leu Asn Gly Asp Gly Gly Val Gly Arg Arg
        50                  55                  60

Arg Leu Trp Ile Gly Leu Gln Leu Pro Pro Gly Cys Gly Asp Pro Lys
65                  70                  75                  80

Arg Leu Gly Pro Leu Arg Gly Phe Gln Trp Val Thr Gly Asp Asn Asn
                85                  90                  95

Thr Ser Tyr Ser Arg Trp Ala Arg Leu Asp Leu Asn Gly Ala Pro Leu
                100                 105                 110

Cys Gly Pro Leu Cys Val Ala Val Ser Ala Ala Glu Ala Thr Val Pro
            115                 120                 125

Ser Glu Pro Ile Trp Glu Glu Gln Gln Cys Glu Val Lys Ala Asp Gly
        130                 135                 140

Phe Leu Cys Glu Phe His Phe Pro Ala Thr Cys Arg Pro
145                 150                 155

<210> SEQ ID NO 3
<211> LENGTH: 31
<212> TYPE: PRT
<213> ORGANISM: Homo sapiens
<220> FEATURE:
<221> NAME/KEY: PEPTIDE
<222> LOCATION: (1)...(31)
<223> OTHER INFORMATION: Human thrombomodulin fragment 3

<400> SEQUENCE: 3

Pro Gln Pro Gly Gly Ser Gln Cys Val Glu His Asp Cys Phe Ala Leu
1               5                   10                  15

Tyr Pro Gly Pro Ala Thr Phe Leu Asn Ala Ser Gln Ile Cys Asp
                20                  25                  30
```

<210> SEQ ID NO 4
<211> LENGTH: 127
<212> TYPE: PRT
<213> ORGANISM: Homo sapiens
<220> FEATURE:
<221> NAME/KEY: PEPTIDE
<222> LOCATION: (1)...(127)
<223> OTHER INFORMATION: Human thrombomodulin fragment 4

<400> SEQUENCE: 4

Asp Gly Leu Arg Gly His Leu Met Thr Val Arg Ser Ser Val Ala Ala
1               5                   10                  15

Asp Val Ile Ser Leu Leu Asn Gly Asp Gly Val Gly Arg Arg
            20                  25                  30

Arg Leu Trp Ile Gly Leu Gln Leu Pro Pro Gly Cys Gly Asp Pro Lys
        35                  40                  45

Arg Leu Gly Pro Leu Arg Gly Phe Gln Trp Val Thr Gly Asp Asn Asn
    50                  55                  60

Thr Ser Tyr Ser Arg Trp Ala Arg Leu Asp Leu Asn Gly Ala Pro Leu
65                  70                  75                  80

Cys Gly Pro Leu Cys Val Ala Val Ser Ala Ala Glu Ala Thr Val Pro
                85                  90                  95

Ser Glu Pro Ile Trp Glu Glu Gln Gln Cys Glu Val Lys Ala Asp Gly
            100                 105                 110

Phe Leu Cys Glu Phe His Phe Pro Ala Thr Cys Arg Pro Leu Ala
        115                 120                 125

<210> SEQ ID NO 5
<211> LENGTH: 23
<212> TYPE: PRT
<213> ORGANISM: Homo sapiens
<220> FEATURE:
<221> NAME/KEY: PEPTIDE
<222> LOCATION: (1)...(23)
<223> OTHER INFORMATION: Human thrombomodulin fragment 5

<400> SEQUENCE: 5

Leu Tyr Pro Gly Pro Ala Thr Phe Leu Asn Ala Ser Gln Ile Cys Asp
1               5                   10                  15

Gly Leu Arg Gly His Leu Met
            20

<210> SEQ ID NO 6
<211> LENGTH: 10
<212> TYPE: PRT
<213> ORGANISM: Homo sapiens
<220> FEATURE:
<221> NAME/KEY: PEPTIDE
<222> LOCATION: (1)...(10)
<223> OTHER INFORMATION: Human thrombomodulin fragment 6

<400> SEQUENCE: 6

Ala Ala Asp Val Ile Ser Leu Leu Leu Asn
1               5                   10

<210> SEQ ID NO 7
<211> LENGTH: 14
<212> TYPE: PRT
<213> ORGANISM: Homo sapiens
<220> FEATURE:
<221> NAME/KEY: PEPTIDE
<222> LOCATION: (1)...(14)
<223> OTHER INFORMATION: Human thrombomodulin fragment 7

<400> SEQUENCE: 7

Pro Leu Arg Gly Phe Gln Trp Val Thr Gly Asp Asn Asn Thr
1               5                   10

<210> SEQ ID NO 8
<211> LENGTH: 38
<212> TYPE: PRT
<213> ORGANISM: Homo sapiens
<220> FEATURE:
<221> NAME/KEY: PEPTIDE
<222> LOCATION: (1)...(38)
<223> OTHER INFORMATION: Human thrombomodulin fragment 8

<400> SEQUENCE: 8

Arg Leu Gly Pro Leu Arg Gly Phe Gln Trp Val Thr Gly Asp Asn Asn
1               5                   10                  15

Thr Ser Tyr Ser Arg Trp Ala Arg Leu Asp Leu Asn Gly Ala Pro Leu
            20                  25                  30

Cys Gly Pro Leu Cys Val
        35

<210> SEQ ID NO 9
<211> LENGTH: 39
<212> TYPE: DNA
<213> ORGANISM: Artificial Sequence
<220> FEATURE:
<223> OTHER INFORMATION: sense primer TM.s1957i

<400> SEQUENCE: 9
gggctctccg cactatgcag cgtggagaat ggtggctgt                      39

<210> SEQ ID NO 10
<211> LENGTH: 39
<212> TYPE: DNA
<213> ORGANISM: Artificial Sequence
<220> FEATURE:
<223> OTHER INFORMATION: antisense primer TM.as287i

<400> SEQUENCE: 10
attctccacg ctgcatagtg cggagagccc caggctagc                      39

<210> SEQ ID NO 11
<211> LENGTH: 30
<212> TYPE: DNA
<213> ORGANISM: Artificial Sequence
<220> FEATURE:
<223> OTHER INFORMATION: sense primer TM.s240

<400> SEQUENCE: 11
ttctgtggtg gcgcctgcag gccacgcccg                                30

<210> SEQ ID NO 12
<211> LENGTH: 57
<212> TYPE: DNA
<213> ORGANISM: Artificial Sequence
<220> FEATURE:
<223> OTHER INFORMATION: antisense primer TM.as2613EO

<400> SEQUENCE: 12
tggactagtt aattaagatc ttcctcgagg cgcgccgttc agctgaaata ttttagc  57

<210> SEQ ID NO 13
<211> LENGTH: 223
<212> TYPE: PRT

<213> ORGANISM: Mus musculus
<220> FEATURE:
<221> NAME/KEY: PEPTIDE
<222> LOCATION: (1)...(223)
<223> OTHER INFORMATION: Aminoterminal amino acid residues of the
      lectin-like domain

<400> SEQUENCE: 13

Ala Lys Leu Gln Pro Thr Gly Ser Gln Cys Val Glu His Glu Cys Phe
 1               5                  10                  15

Ala Leu Phe Gln Gly Pro Ala Thr Phe Leu Asp Ala Ser Gln Ala Cys
                20                  25                  30

Gln Arg Leu Gln Gly His Leu Met Thr Val Arg Ser Ser Val Ala Ala
            35                  40                  45

Asp Val Ile Ser Leu Leu Leu Ser Gln Ser Ser Met Asp Leu Gly Pro
        50                  55                  60

Trp Ile Gly Leu Gln Leu Pro Gln Gly Cys Asp Asp Pro Val His Leu
65                  70                  75                  80

Gly Pro Leu Arg Gly Phe Gln Trp Val Thr Gly Asp Asn His Thr Ser
                85                  90                  95

Tyr Ser Arg Trp Ala Arg Pro Asn Asp Gln Thr Ala Pro Leu Cys Gly
               100                 105                 110

Pro Leu Cys Val Thr Val Ser Thr Ala Thr Glu Ala Ala Pro Gly Glu
           115                 120                 125

Pro Ala Trp Glu Glu Lys Pro Cys Glu Thr Thr Gln Gly Phe Leu
       130                 135                 140

Cys Glu Phe Tyr Phe Thr Ala Ser Cys Arg Pro Leu Thr Val Asn Thr
145                 150                 155                 160

Arg Asp Pro Glu Ala Ala His Ile Ser Ser Thr Tyr Asn Thr Pro Phe
                165                 170                 175

Gly Val Ser Gly Ala Asp Phe Gln Thr Leu Pro Val Gly Ser Ser Ala
               180                 185                 190

Ala Val Glu Pro Leu Gly Leu Glu Leu Val Cys Arg Ala Pro Pro Gly
           195                 200                 205

Thr Ser Glu Gly His Trp Ala Trp Glu Ala Thr Gly Ala Trp Asn
       210                 215                 220

<210> SEQ ID NO 14
<211> LENGTH: 21
<212> TYPE: DNA
<213> ORGANISM: Artificial Sequence
<220> FEATURE:
<223> OTHER INFORMATION: sense primer TM.s99

<400> SEQUENCE: 14
gtctaggttg tgatagaggc t                                           21

<210> SEQ ID NO 15
<211> LENGTH: 22
<212> TYPE: DNA
<213> ORGANISM: Artificial Sequence
<220> FEATURE:
<223> OTHER INFORMATION: antisense primer TM.as1005

<400> SEQUENCE: 15
ggcagaggca tctgggttca tt                                          22

<210> SEQ ID NO 16
<211> LENGTH: 21
<212> TYPE: DNA

```
<213> ORGANISM: Artificial Sequence
<220> FEATURE:
<223> OTHER INFORMATION: sense primer TM.s2520

<400> SEQUENCE: 16
ggctttgggt atttagtcag a                                    21

<210> SEQ ID NO 17
<211> LENGTH: 20
<212> TYPE: DNA
<213> ORGANISM: Artificial Sequence
<220> FEATURE:
<223> OTHER INFORMATION: antisense primer TM.as2700

<400> SEQUENCE: 17
cataaaaccc aggctcaccc                                      20
```